US012694544B2

(12) United States Patent
Enoki et al.

(10) Patent No.: US 12,694,544 B2
(45) Date of Patent: Jul. 28, 2026

(54) IMAGE PROCESSING DEVICE, IMAGE PROCESSING METHOD, AND SURGICAL MICROSCOPE SYSTEM

(71) Applicant: SONY GROUP CORPORATION, Tokyo (JP)

(72) Inventors: Junichiro Enoki, Tokyo (JP); Izumu Hosoi, Tokyo (JP); Tomoyuki Ootsuki, Tokyo (JP); Koji Kashima, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 109 days.

(21) Appl. No.: 18/689,443

(22) PCT Filed: Feb. 22, 2022

(86) PCT No.: PCT/JP2022/007075
§ 371 (c)(1),
(2) Date: Mar. 6, 2024

(87) PCT Pub. No.: WO2023/047626
PCT Pub. Date: Mar. 30, 2023

(65) Prior Publication Data
US 2025/0139795 A1 May 1, 2025

(30) Foreign Application Priority Data

Sep. 21, 2021 (JP) ................................. 2021-153544

(51) Int. Cl.
*G06T 7/33* (2017.01)
*A61B 90/00* (2016.01)
(Continued)

(52) U.S. Cl.
CPC .............. *G06T 7/337* (2017.01); *A61B 90/20* (2016.02); *A61B 90/37* (2016.02); *G06T 3/14* (2024.01);
(Continued)

(58) Field of Classification Search
CPC .. G06T 7/337; G06T 5/90; G06T 5/73; G06T 3/14; G06T 3/20; G06T 3/40;
(Continued)

(56) References Cited

U.S. PATENT DOCUMENTS

2011/0028951 A1* 2/2011 Raksi ...................... A61F 9/008
606/4
2011/0028953 A1* 2/2011 Raksi .................... A61F 9/0084
606/4
(Continued)

FOREIGN PATENT DOCUMENTS

JP 2001-269317 A 10/2001
JP 2004-089215 A 3/2004
(Continued)

OTHER PUBLICATIONS

Filippatos Konstantinos translation of JP2016016331 Feb. 1, 2016 (Year: 2016).*
(Continued)

*Primary Examiner* — Zaihan Jiang
(74) *Attorney, Agent, or Firm* — CHIP LAW GROUP

(57) ABSTRACT

There is provided an image processing device including a displayed-image generation unit that generates a displayed image in which a first reference image indicating reference coordinates of a preoperative image that is a captured image of an eyeball of a patient before surgery is superimposed on the preoperative image, and a second reference image indicating reference coordinates of an intraoperative image that is a captured image of the eyeball of the patient at the start of the surgery or during the surgery is superimposed on the intraoperative image, wherein the displayed-image generation unit arranges the first reference image and the second reference image such that the respective reference coordinates of the preoperative image and the intraoperative image correspond to each other, and such that a scale, a position, (Continued)

or an orientation of at least one of the preoperative image or the intraoperative image is changeable, to generate the displayed image.

17 Claims, 19 Drawing Sheets

(51) Int. Cl.

| | | |
|---|---|---|
| *A61B 90/20* | (2016.01) | |
| *G06T 3/14* | (2024.01) | |
| *G06T 3/20* | (2006.01) | |
| *G06T 3/40* | (2024.01) | |
| *G06T 5/73* | (2024.01) | |
| *G06T 5/90* | (2024.01) | |
| *G06V 10/25* | (2022.01) | |

(52) U.S. Cl.
CPC .................. *G06T 3/20* (2013.01); *G06T 3/40* (2013.01); *G06T 5/73* (2024.01); *G06T 5/90* (2024.01); *G06V 10/25* (2022.01); *G06T 2207/10056* (2013.01); *G06T 2207/30041* (2013.01); *G06T 2207/30101* (2013.01); *G06V 2201/03* (2022.01)

(58) Field of Classification Search
CPC . G06T 2207/10056; G06T 2207/30041; G06T 2207/30101; A61B 90/20; A61B 90/37; G06V 10/25; G06V 2201/03
See application file for complete search history.

(56) References Cited

U.S. PATENT DOCUMENTS

| | | | | |
|---|---|---|---|---|
| 2011/0028957 A1* | 2/2011 | Raksi | .................. | A61F 9/00825 |
| | | | | 606/6 |
| 2011/0028958 A1* | 2/2011 | Raksi | .................. | A61F 9/00825 |
| | | | | 606/6 |
| 2011/0118713 A1* | 5/2011 | Raksi | .................. | A61F 9/00825 |
| | | | | 606/6 |
| 2016/0128654 A1* | 5/2016 | Wollowick | ............. | G16H 20/40 |
| | | | | 600/424 |

FOREIGN PATENT DOCUMENTS

| | | | |
|---|---|---|---|
| JP | 2008-521508 | A | 6/2008 |
| JP | 2011-528592 | A | 11/2011 |
| JP | 2012-506272 | A | 3/2012 |
| JP | 2013-236952 | A | 11/2013 |
| JP | 2014-504177 | A | 2/2014 |
| JP | 2016-016331 | A | 2/2016 |
| JP | 2016016331 | * | 2/2016 |
| WO | 2020/008276 | A1 | 1/2020 |
| WO | WO-2022/249190 | * | 5/2022 |

OTHER PUBLICATIONS

International Search Report and Written Opinion of PCT Application No. PCT/JP2022/007075, issued on May 10, 2022, 11 pages of ISRWO.

* cited by examiner

IMAGE PROCESSING DEVICE, IMAGE PROCESSING METHOD, AND SURGICAL MICROSCOPE SYSTEM

CROSS REFERENCE TO RELATED APPLICATIONS

This application is a U.S. National Phase of International Patent Application No. PCT/JP2022/007075 filed on Feb. 22, 2022, which claims priority benefit of Japanese Patent Application No. JP 22021-153544 filed in the Japan Patent Office on Sep. 21, 2021. Each of the above-referenced applications is hereby incorporated herein by reference in its entirety.

FIELD

The present disclosure relates to an image processing device, an image processing method, and a surgical microscope system.

BACKGROUND

In recent years, as a method for refractive correction in ophthalmology, there has been widely used a method in which an artificial lens called an intraocular lens (IOL) is inserted into an eye to eliminate refractive errors in a crystalline lens or the like, thereby improving visual performance such as visual acuity. Then, as an intraocular lens that is a substitute for a crystalline lens removed by cataract surgery, an intraocular lens that can be inserted into a lens capsule is most widely used. Further, in addition to an IOL inserted into a lens capsule, there are various intraocular lenses such as one that is fixed (indwelled) in a ciliary sulcus or the like (Phakic IOL), for example.

For example, in performing ophthalmic surgery such as cataract surgery, an operator performs the surgery while paying attention so as to have an appropriate incision position or an appropriate incision shape, and an appropriate posture of an implant, such as an intraocular lens to be inserted, with respect to an eye, in light of a preoperative plan, in order to improve visual performance after the surgery. During such surgery, it is required to present information regarding an appropriate incision position, an appropriate incision shape, an appropriate posture of an implant, and the like in a form that makes it easier for the operator to perform the surgery. For example, in order to insert an intraocular lens at a position in accordance with a preoperative plan, a guide indicating an insertion position is superimposed on an image of an eyeball of a patient during the surgery. Thus, the operator checks whether the position and orientation of the patient's eyeball at the time of formulating the preoperative plan match the position and orientation of the patient's eyeball during the surgery, in order to perform the surgery in accordance with the preoperative plan. Then, the following Patent Literature 1 proposes a system that displays an image (preoperative image) of an eyeball of a patient during preoperative planning and an image (intraoperative image) of the eyeball during surgery while superimposing the images on each other such that the respective scales, the respective positions, and the respective orientations match each other.

CITATION LIST

Patent Literature

Patent Literature 1: JP 2008-521508 A

SUMMARY

Technical Problem

However, in the proposed system described above, it is difficult for the operator to easily and accurately check whether the preoperative image and the intraoperative image are appropriately aligned.

Therefore, the present disclosure proposes an image processing device, an image processing method, and a surgical microscope system that make it possible to check easily and accurately check whether two images are appropriately aligned.

Solution to Problem

According to the present disclosure, there is provided an image processing device including a displayed-image generation unit configured to generate a displayed image in which a first reference image indicating reference coordinates of a preoperative image that is a captured image of an eyeball of a patient before surgery is superimposed on the preoperative image, and a second reference image indicating reference coordinates of an intraoperative image that is a captured image of the eyeball of the patient at the start of the surgery or during the surgery is superimposed on the intraoperative image. In the image processing device, the displayed-image generation unit arranges the first reference image and the second reference image such that the respective reference coordinates of the preoperative image and the intraoperative image correspond to each other, and such that a scale, a position, or an orientation of at least one of the preoperative image or the intraoperative image is changeable, to generate the displayed image.

Furthermore, according to the present disclosure, there is provided an image processing method including generating, in an image processing device, a displayed image in which a first reference image indicating reference coordinates of a preoperative image that is a captured image of an eyeball of a patient before surgery is superimposed on the preoperative image, and a second reference image indicating reference coordinates of an intraoperative image that is a captured image of the eyeball of the patient at the start of the surgery or during the surgery is superimposed on the intraoperative image. In the image processing method, the generating the displayed-image includes arranging the first reference image and the second reference image such that the respective reference coordinates of the preoperative image and the intraoperative image correspond to each other, and such that a scale, a position, or an orientation of at least one of the preoperative image or the intraoperative image is changeable, to generate the displayed image.

Furthermore, according to the present disclosure, there is provided a surgical microscope system including: a surgical microscope configured to acquire an operative-field image for an eye of a patient; an image processing device configured to generate a displayed image on the basis of the operative-field image; and a display unit configured to display the displayed image. In the surgical microscope system, the image processing device includes a displayed-image generation unit configured to generate the displayed image in which a first reference image indicating reference coordinates of a preoperative image that is a captured image of an eyeball of the patient before surgery is superimposed on the preoperative image, and a second reference image indicating reference coordinates of an intraoperative image that is a captured image of the eyeball of the patient at the start of the surgery or during the surgery is superimposed on the intraoperative image, and the displayed-image generation unit arranges the first reference image and the second reference image such that the respective reference coordinates of the preoperative image and the intraoperative image correspond to each other, and such that a scale, a position, or an orientation of at least one of the preoperative image or the intraoperative image is changeable, to generate the displayed image.

BRIEF DESCRIPTION OF DRAWINGS

FIG. 12 is a view illustrating an example (Part 4) of a displayed image according to a modification of the first embodiment of the present disclosure.

FIG. 13 is a view illustrating an example (Part 5) of a displayed image according to a modification of the first embodiment of the present disclosure.

FIG. 14 is a view illustrating an example (Part 1) of a displayed image according to a second embodiment of the present disclosure.

FIG. 16 is a view illustrating an example (Part 3) of a displayed image according to the second embodiment of the present disclosure.

FIG. 17 is a view illustrating an example (Part 1) of a displayed image according to a third embodiment of the present disclosure.

FIG. 18 is a view illustrating an example (Part 2) of a displayed image according to the third embodiment of the present disclosure.

DESCRIPTION OF EMBODIMENTS

Figure 1:
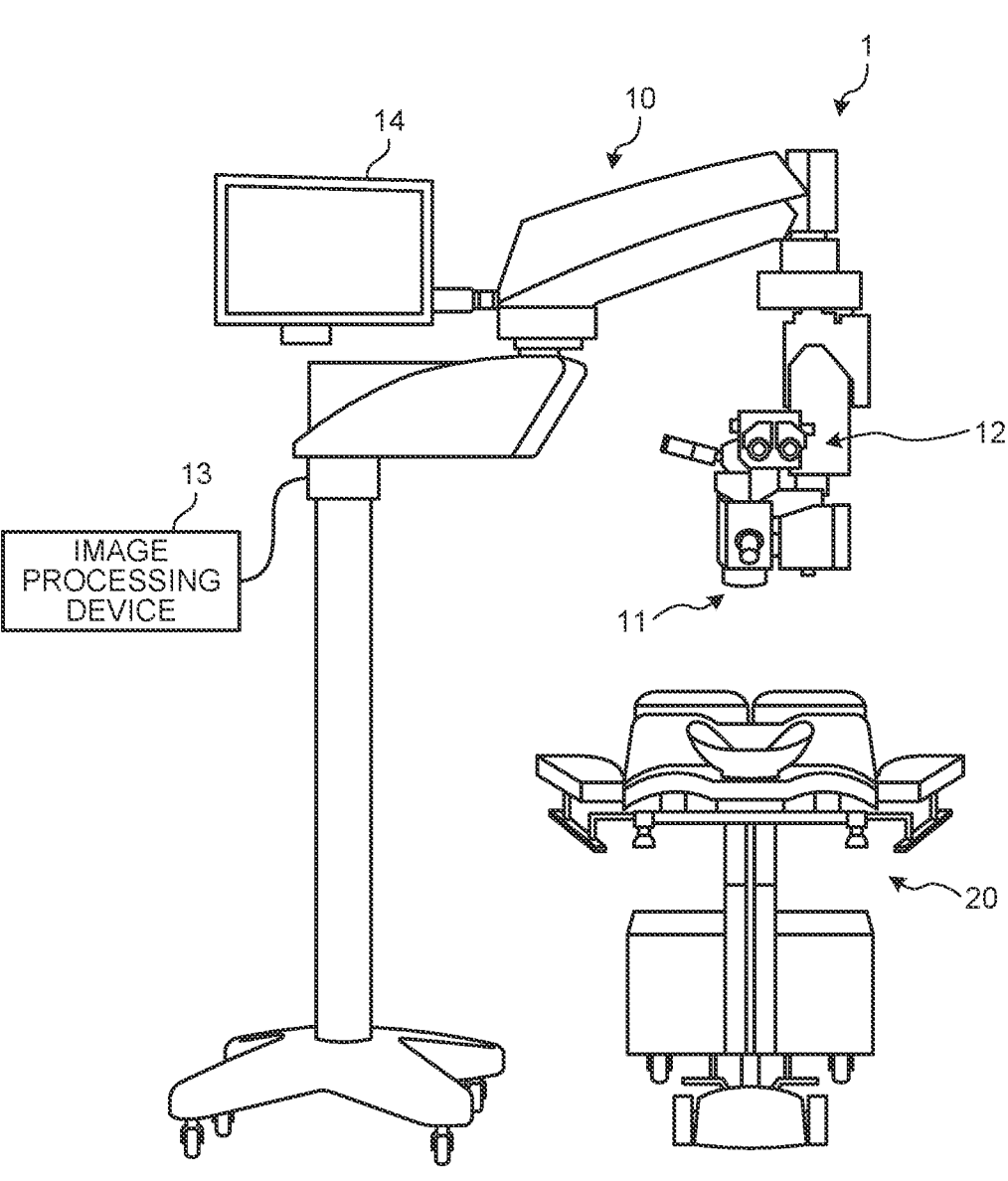
FIG. 1 is a view illustrating an example of a schematic configuration of a surgical microscope system 1 according to embodiments of the present disclosure.

Below, preferred embodiments of the present disclosure will be described in detail with reference to the accompanying drawings. Note that, in the present specification and the drawings, components having substantially the same functional configurations are denoted by the same reference signs, and duplicated description is omitted. Further, in the present specification and the drawings, a plurality of components having substantially the same or similar functional configurations are distinguished by different alphabets at the ends of the same reference signs, in some portions. However, a plurality of components having substantially the same or similar functional configurations are denoted by only the same reference signs unless they need to be specifically distinguished from each other.

The description will be given in the following order.
1. Background leading to creation of embodiments of the present disclosure
   1.1 Example of schematic configuration of surgical microscope system 1
   1.2 Example of schematic configuration of surgical microscope 10
   1.3 Schematic configuration of image processing device 13
   1.4 Background
2. First embodiment
   2.1 Image processing method
   2.2 Displayed image
   2.3 Modifications
3. Second embodiment
4. Third embodiment
5. Conclusion
6. Example of schematic configuration of computer
7. Supplementary notes Note that, in the following description, a preoperative image means an image of a surgery site such as an eyeball or the like of a patient, used in formulating a preoperative plan, and an image of a surgery site, captured in a situation similar to a situation in which the preoperative plan is formulated (for example, a case in which images are captured by different devices while a patient is sitting down in the same manner). An intraoperative image means an image of the eyeball of the patient at the time when surgery is started according to the formulated preoperative plan, or an image of the eyeball of the patient during the surgery.

1. Background Leading to Creation of Embodiments of the Present Disclosure

<1.1 Example of Schematic Configuration of Surgical Microscope System 1>

First, before describing details of the embodiments of the present disclosure, an example of a schematic configuration of a surgical microscope system 1 according to the embodiments of the present disclosure will be described with reference to FIG. 1. FIG. 1 is a view illustrating an example of a schematic configuration of the surgical microscope system 1 according to the embodiments of the present disclosure.

The surgical microscope system 1 according to the embodiments of the present disclosure is a system used for eye surgery, and mainly includes a surgical microscope 10 and a patient bed 20 as illustrated in FIG. 1. A patient undergoes surgery on an eyeball while lying on the patient bed 20. Further, an operator who is a surgeon (also referred to as a user in the present specification) performs surgery while observing the eyeball of the patient with the surgical microscope 10. Below, overviews of respective components of the surgical microscope system 1 according to the embodiments of the present disclosure will be sequentially given.

(Surgical Microscope 10)

As illustrated in FIG. 1, the surgical microscope 10 mainly includes an objective lens 11, an eyepiece 12, an image processing device 13, and a monitor 14. The objective lens 11 and the eyepiece 12 are lenses for enlarging and observing an eyeball of a patient to be subjected to surgery. Further, the image processing device 13 can output various images, various kinds of information, and the like by performing predetermined image processing on an image captured through the objective lens 11. Moreover, the monitor 14 can display an image captured through the objective lens 11, or various images, various kinds of information, and the like generated by the image processing device 13. Note that, in the present embodiments, the monitor 14 may be provided integrally with, or separately from, the surgical microscope 10. Meanwhile, an example of a configuration of the surgical microscope 10 will be described later.

In the surgical microscope system 1, for example, the operator performs surgery while looking into the eyepiece 12 and observing an eyeball of a patient through the objective lens 11. Further, the operator may perform surgery while checking various images (for example, an image before image processing, an image after image processing, and the like), various kinds of information, and the like that are displayed on the monitor 14.

Note that the surgical microscope system 1 according to the present embodiments is not limited to the configuration illustrated in FIG. 1, and may include other devices and the like. For example, the surgical microscope system 1 according to the present embodiments may include a robot arm (not illustrated) or the like that moves in line with an operation of an operator at a remote place so that the operator at a place away from a patient can perform surgery remotely while checking various images.

<1.2 Example of Schematic Configuration of Surgical Microscope 10>

Figure 2:
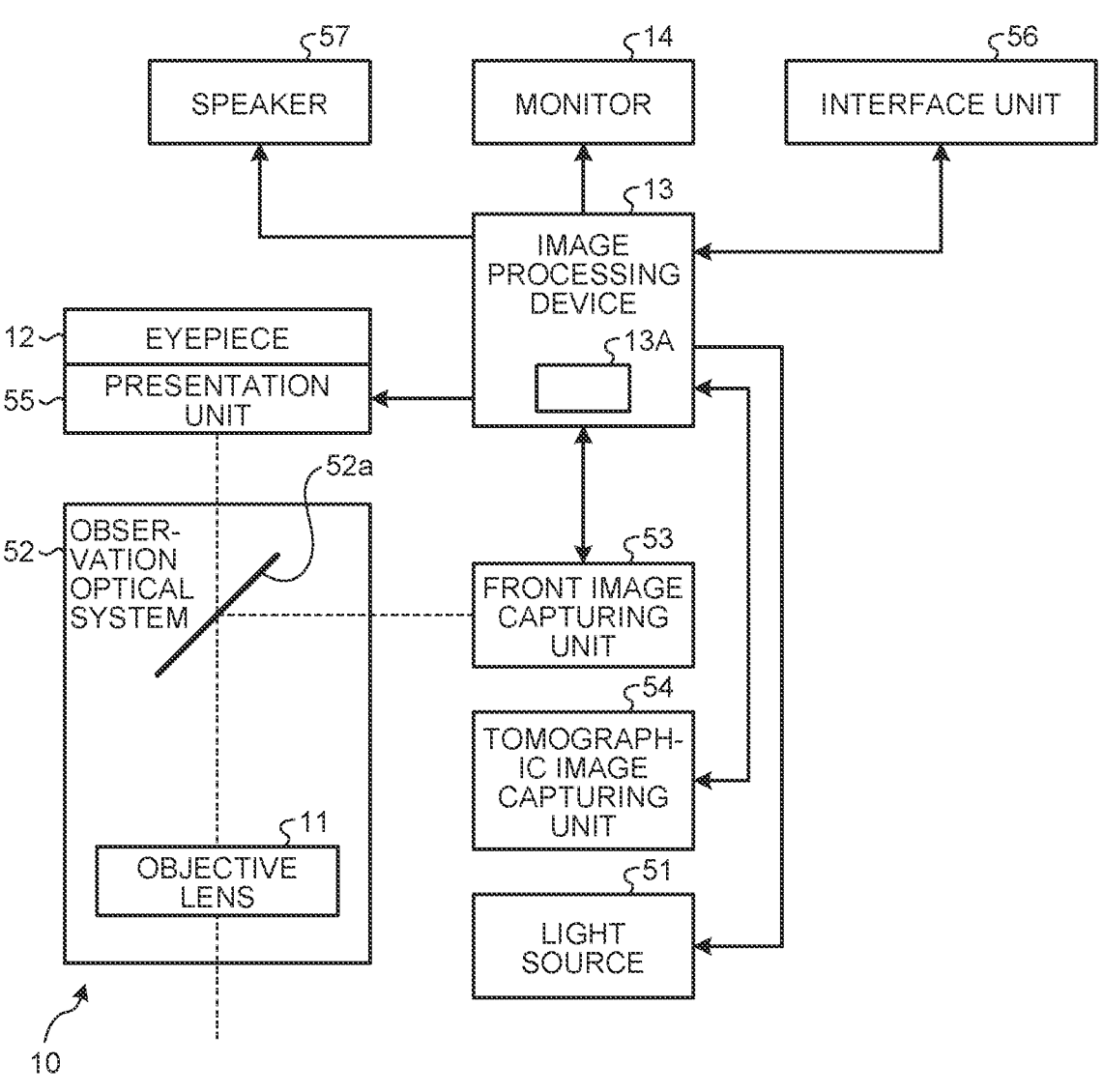
FIG. 2 is a view illustrating an example of a schematic configuration of a surgical microscope 10 according to the embodiments of the present disclosure.

Further, an example of a schematic configuration of the surgical microscope 10 will be described with reference to FIG. 2. FIG. 2 is a view illustrating an example of a schematic configuration of the surgical microscope 10 according to the embodiments of the present disclosure. As illustrated in FIG. 2, the surgical microscope 10 includes a light source 51, an observation optical system 52, a front image capturing unit 53, a tomographic image capturing unit 54, a presentation unit 55, an interface unit 56, and a speaker 57, in addition to the objective lens 11, the eyepiece 12, the image processing device 13, and the monitor 14 described above. Note that the monitor 14 and the presentation unit 55 correspond to a display device. Below, overviews of respective components of the surgical microscope 10 according to the present embodiments will be sequentially given.

(Light Source 51)

The light source 51 can emit illumination light under the control of a control unit 13A included in the image processing device 13, to illuminate an eyeball of a patient.

(Observation Optical System 52)

The observation optical system 52 includes, for example, optical elements such as the objective lens 11, a half mirror 52*a*, and a lens (not illustrated), and can guide light (observation light) reflected from an eyeball of a patient, toward the eyepiece 12 and the front image capturing unit 53. Specifically, light reflected from the eyeball of the patient is incident upon the half mirror 52*a* through the objective lens 11 or the like, as observation light. About a half of the observation light incident upon the half mirror 52*a* directly passes through the half mirror 52*a*, and is incident upon the eyepiece 12 through the presentation unit 55 of a transmission type. Meanwhile, the other half of the observation light incident upon the half mirror 52*a* is reflected from the half mirror 52*a* and is incident upon the front image capturing unit 53.

(Front Image Capturing Unit 53)

The front image capturing unit 53 includes, for example, a video camera or the like. The front image capturing unit 53 receives and photoelectrically converts observation light incident from the observation optical system 52, thereby capturing a front image that is an image of a patient's eyeball observed from the front, in other words, an image of a patient's eyeball captured from an approximate eye-axis direction. More specifically, the front image capturing unit 53 captures a front image under the control of the image processing device 13, and supplies the acquired front image to the image processing device 13.

(Tomographic Image Capturing Unit 54)

The tomographic image capturing unit 54 includes, for example, an optical coherence tomography (OCT) device, a Scheimpflug camera, or the like. Under the control of the image processing device 13, the tomographic image capturing unit 54 can capture a tomographic image that is an image of a cross section of an eyeball of a patient, and supply the acquired tomographic image to the image processing device 13. Here, the tomographic image means an image of a cross section along a direction substantially parallel to the eye-axis direction in the eyeball of the patient. Meanwhile, for example, the tomographic image capturing unit 54 acquires a tomographic image by the interference principle using infrared light. At that time, the optical path of the infrared light and a part of the optical path of observation light in the observation optical system 52 may be the same with each other.

(Eyepiece 12)

The eyepiece 12 can collect observation light incident from the observation optical system 52 through the presentation unit 55 and form an optical image of an eyeball of a patient. Then, as the eyepiece 12 forms an optical image of the patient's eyeball, the operator who is looking into the eyepiece 12 can observe the patient's eyeball.

(Presentation Unit 55)

The presentation unit 55 includes a transmission display device or the like, and is placed between the eyepiece 12 and the observation optical system 52. The presentation unit 55 can transmit observation light incident from the observation optical system 52 and causes the observation light to enter the eyepiece 12, and further, can present (display) various images (for example, a front image, a tomographic image, and the like) and various kinds of information supplied from the image processing device 13 as necessary. Note that, in the present embodiments, various images, various kinds of information, and the like may be, for example, presented while being superimposed on an optical image of an eyeball of a patient, or presented in a peripheral portion of the optical image so as not to obstruct the optical image.

(Image Processing Device 13)

The image processing device 13 includes the control unit 13A that controls the operation of the surgical microscope 10 as a whole. For example, the control unit 13A can change an illuminating condition of the light source 51 or change a zoom ratio of the observation optical system 52. Further, the control unit 13A can control image acquisition of the front image capturing unit 53 and the tomographic image capturing unit 54 on the basis of information about an operator's operation, supplied from the interface unit 56, or the like. Meanwhile, an example of a configuration of the image processing device 13 will be described later.

(Interface Unit 56)

The interface unit 56 includes, for example, a communication unit (not illustrated) or the like. The communication unit can receive an instruction from an operation unit such as a touch panel, a controller, a remote controller, or an operation stick (not illustrated) superimposed on the monitor 14, or can receive such an instruction with a microphone (not illustrated) capable of receiving an instruction by voice of an operator. For example, the operator can easily adjust an image or the like displayed on the monitor 14 by operating the touch panel superimposed on the monitor 14. Further, the interface unit 56 can supply information or the like corresponding to an operation of the operator or the like, to the image processing device 13. In addition, the interface unit 56 can output device control information for controlling an external device, or the like, supplied from the image processing device 13, to the external device.

(Monitor 14)

The monitor 14 can display various images such as a front image and various kinds of information on a display screen under the control of the control unit 13A of the image processing device 13. Further, in the present embodiments, as described above, a touch panel that receives an operation of the operator may be superimposed on the monitor 14.

(Speaker 57)

For example, in a case where a dangerous situation is detected during surgery, the speaker 57 can output a sound such as a buzzer sound or a melody sound, a message (voice), or the like in order to notify the operator or the like of the dangerous situation, under the control of the control unit 13A of the image processing device 13. Note that, in the present embodiments, the surgical microscope 10 may include a rotary lamp or an indicator lamp (lamp) for notifying an operator or the like of a dangerous situation by blinking, and a vibrator for notifying the operator or the like of a dangerous situation by vibration.

In the surgical microscope system 1 described above, the operator performs fine alignment and posture setting of an implant such as an intraocular lens using a guide based on an ophthalmic surgery guidance formulated in accordance with a preoperative plan, as a reference, to thereby achieve surgery in accordance with the preoperative plan with high accuracy.

Note that the surgical microscope 10 according to the present embodiments is not limited to the configuration illustrated in FIG. 2, and, for example, may include a plurality of monitors 14, a plurality of speakers 57, and the like.

<1.3 Schematic Configuration of Image Processing Device 13>

Figure 3:
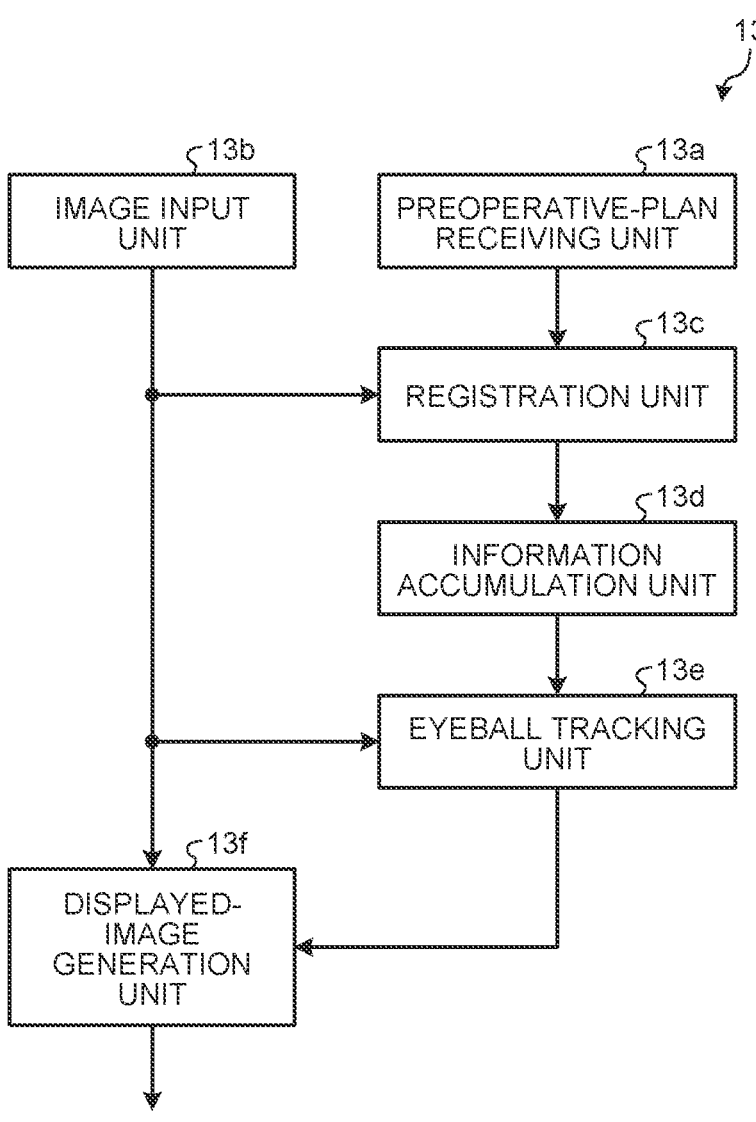
FIG. 3 is a view illustrating an example of a schematic configuration of an image processing device 13 according to the embodiments of the present disclosure.

Next, an example of a schematic configuration of the image processing device 13 according to the present embodiments will be described with reference to FIG. 3. FIG. 3 is a view illustrating an example of a schematic configuration of the image processing device 13 according to the embodiments of the present disclosure. As illustrated in FIG. 3, the image processing device 13 according to the embodiments of the present disclosure mainly includes a preoperative-plan receiving unit 13a, an image input unit (image acquisition unit) 13b, a registration unit 13c, an information accumulation unit 13d, an eyeball tracking unit 13e, and a displayed-image generation unit 13f. Below, overviews of the respective components of the image processing device 13 according to the present embodiments will be sequentially given.

(Preoperative-Plan Receiving Unit 13a)

The preoperative-plan receiving unit 13a can acquire preoperative-plan information (for example, a preoperative image in a preoperative plan, guide (mark) posture information based on a preoperative plan, and the like) for an eye of a patient. Note that, in the present embodiments, the guide posture information described above includes information (size information, position information, orientation information, and the like) regarding a scale (size) of the guide with respect to a corneal limbus or the like in a preoperative image, a position of the guide, and an orientation of the guide around an eye axis (a position of a direction of rotation around the eye axis). For example, the orientation around the eye axis is defined by an angle to a direction of rotation around the eye axis with respect to a reference line orthogonal to the eye axis. Meanwhile, both the position of the coordinates of the guide and the position of the direction of rotation around the eye axis correspond to guide position information.

(Image Input Unit 13b)

The image input unit 13b can acquire operative-field images (front images) including a preoperative image before the start of surgery, an intraoperative image during surgery, and the like from the front image capturing unit 53 (see FIG. 2), and supply these operative-field images to the registration unit 13c, the eyeball tracking unit 13e, the displayed-image generation unit 13f, and the like described later.

(Registration Unit 13c)

The registration unit 13c can obtain a correspondence between a preoperative image and an intraoperative image such as a difference in scale (size), a deviation amount, and a deviation direction, for example, by comparing the preoperative image and the intraoperative image. Then, the registration unit 13c can supply deviation information (registration information) regarding a difference in scale, a deviation amount, and a deviation direction, together with the above-described operative-field images, to the information accumulation unit 13d and the displayed-image generation unit 13f.

For example, the registration unit 13c obtains a correspondence between respective pixels of the preoperative image and the intraoperative image by image recognition, thereby acquiring registration information that is information about deviation between these two operative-field images. More specifically, for example, the registration unit 13c can extract a plurality of feature points common to the two operative-field images, and obtain deviation between the two operative-field images as a whole on the basis of the deviation between corresponding feature points of the two operative-field images. Note that it is possible to obtain deviation between the two operative field-images as a whole by using the correspondences between all the pixels of the two operative-field images, but to do so increases the processing load. Thus, deviation is obtained using a common feature point, which can prevent an increase in the processing load.

Note that, as the feature point, for example, a pattern of a blood vessel, a scar, or the like in an eyeball of a patient, an edge of a corneal limbus, or the like can be used, and the operator may determine in advance which feature point to use. Alternatively, in the present embodiments, the above-described feature point may be automatically extracted from an operative-field image by image recognition using an algorithm acquired by learning in which an image of the above-described feature point is learned by machine learning.

In the present embodiments, by using the registration information acquired by the registration unit 13c, it is possible to accurately match two different operative-field images (a preoperative image and an intraoperative image) with one coordinate set. Note that, in the present embodiments, a method for acquiring the registration information is not limited to the above-described method, and various existing methods can be used.

(Information Accumulation Unit 13d)

The information accumulation unit 13d can convert the guide (mark) posture information in accordance with an intraoperative image that is an operative-field image at the start of surgery, on the basis of the registration information (deviation information) supplied from the registration unit 13c and the intraoperative image, and can accumulate therein the intraoperative image and the guide posture information having been converted in accordance with the intraoperative image.

(Eyeball Tracking Unit 13e)

The eyeball tracking unit 13e can track an eyeball of a patient during surgery by sequentially comparing a plurality of operative-field images (intraoperative images) acquired during surgery from the start of the surgery. Further, the eyeball tracking unit 13e can supply displacement information indicating a difference (for example, a deviation amount and a deviation direction) between eyeball posture information in the intraoperative image and the guide (mark) posture information accumulated in the information accumulation unit 13d, to the displayed-image generation unit 13f. Like the guide posture information, the eyeball posture information includes information (size information, position information, orientation information, and the like) regarding a size of the eyeball, a position of the eyeball, and an orientation of the eyeball around the eye axis (a position of a direction of rotation around the eye axis). Meanwhile, both the position of the coordinates of the eyeball and the position of the direction of rotation around the eye axis correspond to eyeball position information.

(Displayed-Image Generation Unit 13f)

On the basis of a correspondence (registration information) between a preoperative image at the time of preoperative planning and an intraoperative image at the start of surgery, acquired by the registration unit 13c, the displayed-image generation unit 13f adjusts the postures (scales (sizes), positions, orientations, and the like) of these two operative-field images and reference coordinates described later so as to eliminate deviation between the preoperative image and the intraoperative image. Further, the displayed-image generation unit 13f can generate a displayed image by superimposing a mark or the above-described reference coordinates on these two operative-field images. Specifically, the displayed-image generation unit 13f can turn, translate, enlarge, and reduce the preoperative image and the intraoperative image. Further, the displayed-image generation unit 13f can turn, translate, enlarge, and reduce the reference coordinates superimposed on the preoperative image and the intraoperative image. Moreover, the displayed-image generation unit 13f can also adjust contrast, sharpness, color, brightness, and the like of the preoperative image and the intraoperative image. Details of the reference coordinates will be described later.

Note that the image processing device 13 according to the present embodiments is not limited to the example illustrated in FIG. 3, and may further include another functional unit, for example.

<1.4 Background>

Next, the background that has led the present inventors to create the embodiments of the present disclosure and overview of the embodiments of the present disclosure will be described.

In an ophthalmic surgery guidance, a preoperative image used in formulating a preoperative plan and an intraoperative image acquired at the start of surgery are aligned on the basis of deviation between the preoperative image and the intraoperative image. Then, in the guidance, a guide for creation of a wound, incision of an anterior capsule, axial alignment of a toric IOL (intraocular lens for correcting astigmatism), centering of an IOL, and the like in accordance with the preoperative plan is superimposed on the intraoperative image and displayed. Then, the operator performs surgery according to the preoperative plan while referring to the guide. Therefore, as described above, in order to perform the surgery according to the preoperative plan with high accuracy, the operator checks whether the alignment is appropriately performed. For example, the operator grasps a pattern of a blood vessel or a scar of a patient's eyeball common to the preoperative image and the intraoperative image, and checks whether the alignment is appropriately performed on the basis of the scale (size), position, and orientation of the pattern.

In addition, for cataract surgery and the like using the ophthalmic surgery guidance, it takes such short time as about 10 minutes to perform surgery once, and hence there is a need to minimize time taken to check such alignment as described above.

Then, as described above, in the system proposed in the above-described Patent Literature 1, an image (preoperative image) of an eyeball of a patient during preoperative planning and an image (intraoperative image) of the eyeball during surgery are displayed while being superimposed on each other such that the respective scales, the respective positions, and the respective orientations match each other.

However, in the above-described system, an image in which the preoperative image and the intraoperative image are displayed while being superimposed at a fixed blend ratio is provided, and thus it is difficult for an operator to visually recognize a pattern of a blood vessel, a scar, or the like included in each operative-field image (the preoperative image and the intraoperative image) for each operative-field image. Further, in the above-described system, even in a case where the blend ratio is adjusted, only a pattern of a blood vessel, a scar, or the like included in one operative-field image can be visually recognized at a time. Thus, whether there is a pattern or the like common to the two operative-field images, and whether the scales, positions, and orientations of the respective patterns or the like match are determined on the basis of the memory of the operator.

Therefore, it is difficult for the operator to easily and accurately check whether the preoperative image and the intraoperative image are appropriately aligned, using the images provided by the above-described system.

Then, in view of the above-described situation, the present inventors have created the embodiments of the present disclosure that make it possible to easily and accurately check whether the preoperative image and the intraoperative image are appropriately aligned.

In the embodiments of the present disclosure, the postures (scales (sizes), positions, orientations, and the like) of the preoperative image and the intraoperative image are matched on the basis of information (registration information) about deviation between the preoperative image and the intraoperative image, and these two operative-field images (the preoperative image and the intraoperative image) are arranged and displayed. In addition, in the present embodiments, the reference coordinates serving as a reference for comparing the above-described two operative-field images are displayed while being superimposed on these operative-field images. Thus, according to the present embodiments, the preoperative image and the intraoperative image are arranged and displayed, which allows the operator to easily grasp the position and posture of the pattern of a blood vessel or a scar of the patient's eyeball common to the preoperative image and the intraoperative image, in each operative-field image. Further, in the present embodiments, the common reference coordinates are displayed while being superimposed on the preoperative image and the intraoperative image, which allows the operator to more easily grasp the posture of the pattern of a blood vessel or a scar of the patient's eyeball using the reference coordinates as a reference. Consequently, according to the present embodiments, the operator can easily and accurately check whether the preoperative image and the intraoperative image are appropriately aligned. This results in reduction of time and effort for checking whether the position of the above-described guide is appropriate, to thereby eliminate troubles.

Below, details of the embodiments of the present disclosure will be sequentially given.

2. First Embodiment

<2.1 Image Processing Method>

Figure 4:
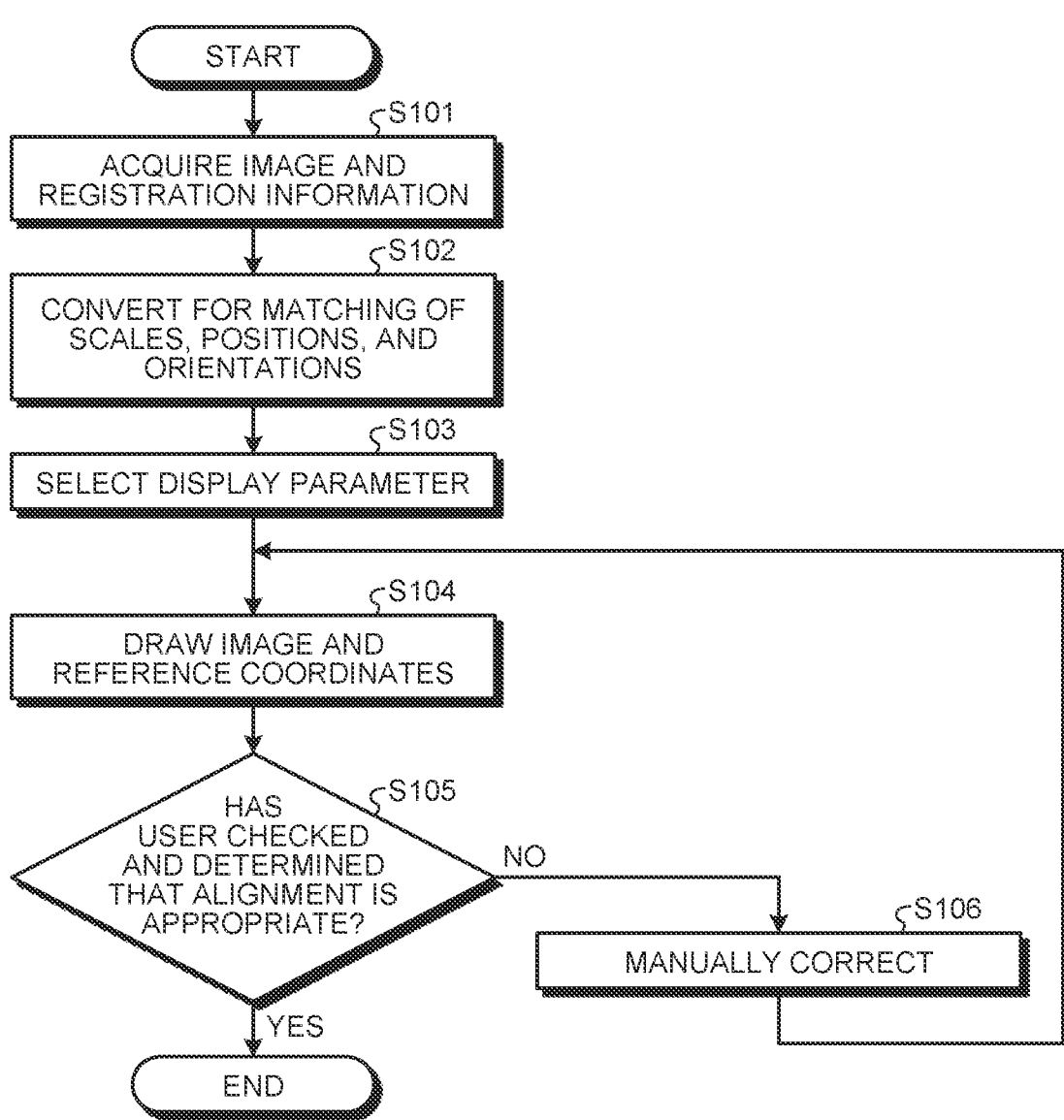
FIG. 4 is a flowchart illustrating an example of an information processing method according to a first embodiment of the present disclosure.

First, an example of a flow of an image processing method according to a first embodiment of the present disclosure will be described with reference to FIG. 4. FIG. 4 is a flowchart illustrating an example of the information processing method according to the embodiment of the present disclosure. Note that the image processing method according to the first embodiment of the present disclosure is performed in the above-described image processing device 13 according to the embodiments of the present disclosure.

Specifically, as illustrated in FIG. 4, the image processing method according to the present embodiment can mainly include a plurality of steps from Step S101 to Step S106. Below, details of those steps according to the present embodiment will be sequentially described.

First, the image processing device 13 acquires a preoperative image and an intraoperative image, and compares the preoperative image and the intraoperative image that have been acquired, to acquire information (registration information) about deviation in scale (size), position, and orientation between the two operative-field images (Step S101).

Secondly, the image processing device 13 turns, translates, enlarges, or reduces one or both of the two operative-field images (the preoperative image and the intraoperative image) on the basis of the registration information acquired in Step S101 described above, and performs image conversion so that the respective scales, the respective positions, and the respective orientations of the both images match each other (specifically, the respective scales and the respective orientations of the reference coordinates of the both operative-field images match each other) (Step S102).

Then, the image processing device 13 selects whether to perform image processing (contrast conversion, color adjustment, brightness adjustment, edge enhancement processing, conversion to vascular structure image, or the like)

on the operative-field images in order to facilitate visual recognition of a pattern of a blood vessel, a scar, or the like of a patient's eyeball included in each of the two operative-field images (the preoperative image and the intraoperative image). In a case where the image processing device 13 selects to perform the above-described image processing, the image processing device 13 selects a display parameter indicating a degree to which the image processing is to be performed (Step S103). In the present embodiment, by performing such image processing, it is possible to easily grasp a position, an orientation, and the like of a feature point (for example, a pattern of a blood vessel or a scar, or the like) common to the two operative-field images.

In the present embodiment, the above-described display parameter may be selected by the operator, or may be automatically selected on the basis of a result of analysis (recognition) performed on the operative-field images. Further, in Step S103, the image processing device 13 receives a selection input instruction in which the operator has selected whether to arrange the two operative-field images (the preoperative image and the intraoperative image) having been subjected to the image processing along the longitudinal direction or along the horizontal direction of the display screen of the display device (monitor) 14, for display. In this manner, in the present embodiment, a display form for the operative-field images can be selected in accordance with the preference of the operator, the operative method, or the like.

Subsequently, the image processing device 13 performs image processing for facilitating visual recognition of a feature point (for example, a pattern of a blood vessel, a scar, or the like) common to the two operative-field images (the preoperative image and the intraoperative image) on the basis of the display parameter selected in Step S103 described above. Moreover, the image processing device 13 sets an origin of the reference coordinates at each of positions corresponding to each other on the respective operative-field images on the basis of the registration information. For example, the image processing device 13 sets the origin at the center of the corneal limbus of the eyeball, the center of a pupil, the position of a corneal vertex, or the like. Then, the image processing device 13 draws such that the reference coordinates (first and second reference images) are superimposed on each of the two operative-field images, on the basis of the position of the origin having been set (Step S104). In the present embodiment, a reference coordinate system can be, for example, in the form of ring-shaped coordinates, polar coordinates, or coordinates having a spider-web grid or a grid representing XY coordinates, details of which will be described later. Note that, in the present embodiment, the image processing device 13 draws each reference image such that the respective scales and orientations of the reference coordinates superimposed on the operative-field images match each other, for example.

Further, the image processing device 13 displays the two operative-field images (the preoperative image and the intraoperative image) in which the reference coordinates are drawn while arranging the images along the direction (predetermined direction) selected in Step S103 described above. For example, the two operative-field images are arranged along the longitudinal direction or the horizontal direction of the display screen of the display device (monitor) 14. In the present embodiment, when the images are arranged along the longitudinal direction, it is preferable that the respective origins of the reference coordinates on the two operative-field images are positioned on the same straight line along the longitudinal direction. On the other hand, in the present embodiment, when the images are arranged along the horizontal direction, it is preferable that the respective origins of the reference coordinates on the two operative-field images are positioned on the same straight line along the horizontal direction. In the present embodiment, the origins of the reference coordinates are aligned with each other as described above, which makes it easy to check the position of a feature point, such as a scar or a blood vessel, common to the two operative-field images.

Further, the operator (user) checks whether the common feature points, such as a blood vessel or a scar, of the two operative-field images are at the same position and have the same orientation, on the basis of the relative positional relationship with the reference coordinates in the two operative-field images (the preoperative image and the intraoperative image) being arranged, to thereby determine whether the two operative-field images are appropriately aligned (Step S105). In a case where the operator determines that the two operative-field images are appropriately aligned (Step S105: Yes), the series of steps of the image processing method ends. On the other hand, in a case where the operator determines that the two operative-field images are not appropriately aligned (Step S105: No), the flow proceeds to Step S106 described later.

Subsequently, the scales (sizes), positions, and orientations of the two operative-field images or the reference coordinates are manually corrected so that the two operative-field images (the preoperative image and the intraoperative image) are appropriately aligned (Step S106). At that time, the image processing device 13 turns, translates, enlarges, or reduces the operative-field images or the reference coordinates in accordance with an instruction for correction from the operator.

Specifically, in Step S105 described above, one of reasons why the operator determines that the two operative-field images are not appropriately aligned is that whether the positions and orientations of the common feature points match each other cannot be checked due to deviation between the scales of the two operative-field images or the origins of the reference coordinates. In such a case, the operator manually corrects the scales, positions, and orientations of the two operative-field images, or the scales, positions, or orientations of the reference coordinates. Further, as another reason, there is cited a difference in orientation between the two operative-field images despite matching of the scales of the two operative-field images and matching of the origins of the reference coordinates. In such a case, the operator manually corrects the orientations of the two operative-field images.

More specifically, the operator performs an operation such as dragging or swiping on the displayed operative-field images (the preoperative image and the intraoperative image), to translate or turn the images, thereby correcting the positions and the orientations. Further, the operator may designate a tissue or a region (for example, corneal limbus) serving as a reference by tracing the outlines of the tissue or region with a finger on the displayed operative-field images, and pinch in or out the designated region, thereby correcting the scales.

Then, the image processing devices 13 returns to Step S104 described above, and repeats Steps S104, S105, and S106, thereby displaying two appropriately-aligned operative-field images (the preoperative image and the intraoperative image).

Note that the respective steps in the processing of the present embodiment described above are not necessarily required to be performed in the described order, and the steps may be performed in an order that is appropriately changed or a part of the steps may be performed in parallel.

<2.2 Displayed Image>

Figure 5:
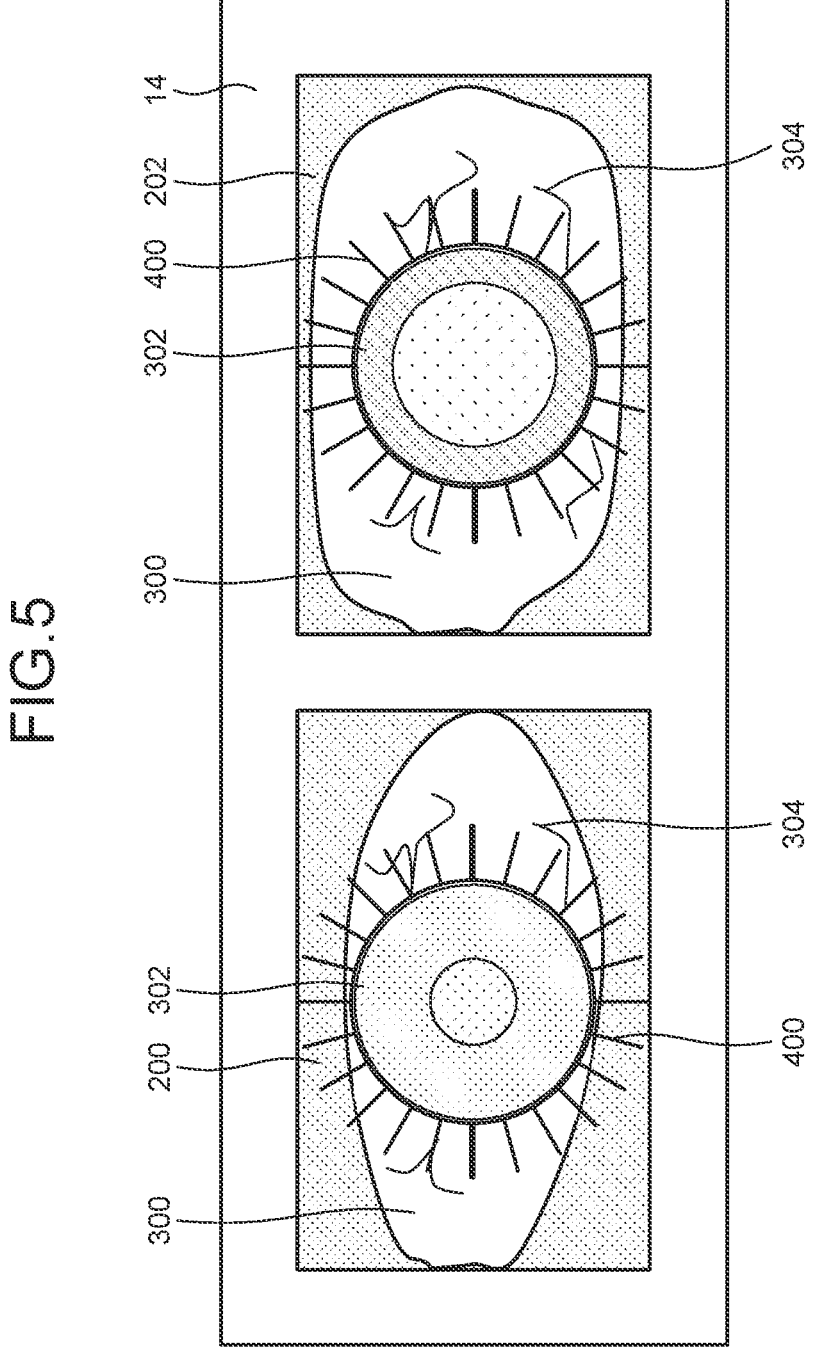
FIG. 5 is a view illustrating an example (Part 1) of a displayed image according to the first embodiment of the present disclosure.
Figure 6:
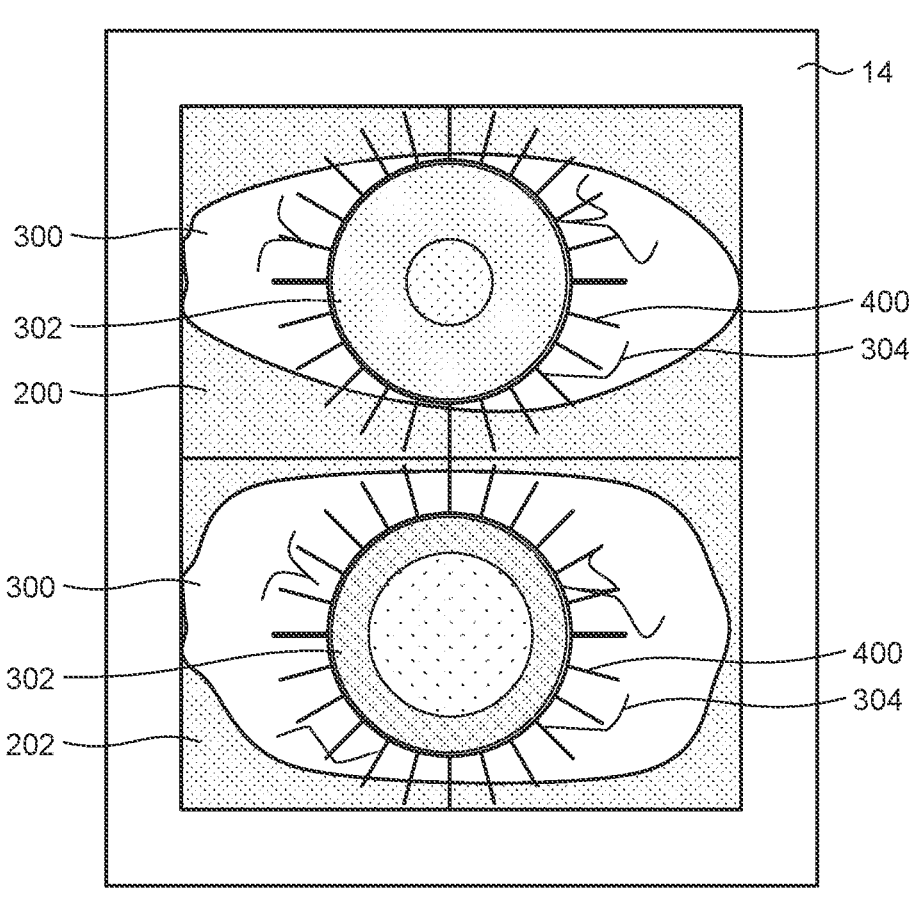
FIG. 6 is a view illustrating an example (Part 2) of a displayed image according to the first embodiment of the present disclosure.
Figure 7:
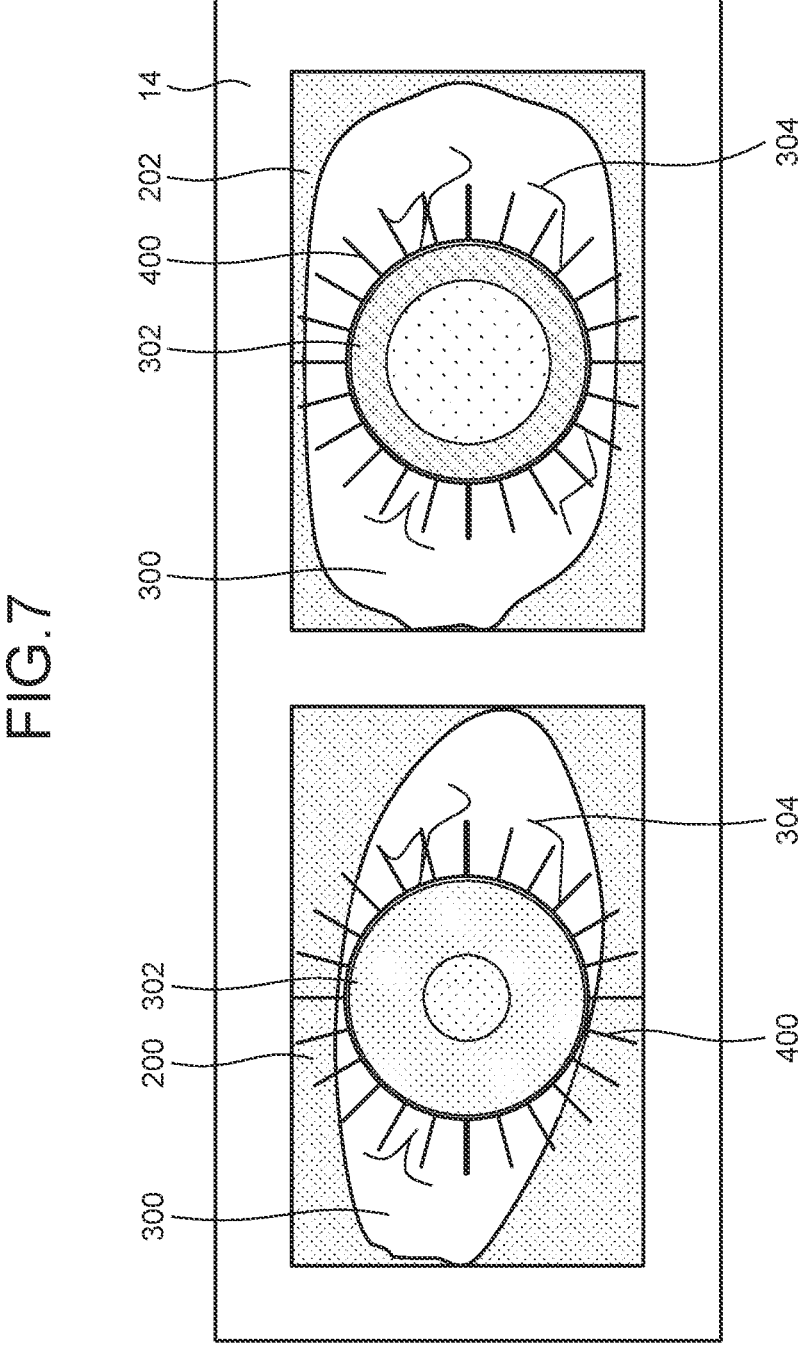
FIG. 7 is a view illustrating an example (Part 3) of a displayed image according to the first embodiment of the present disclosure.
Figure 8:
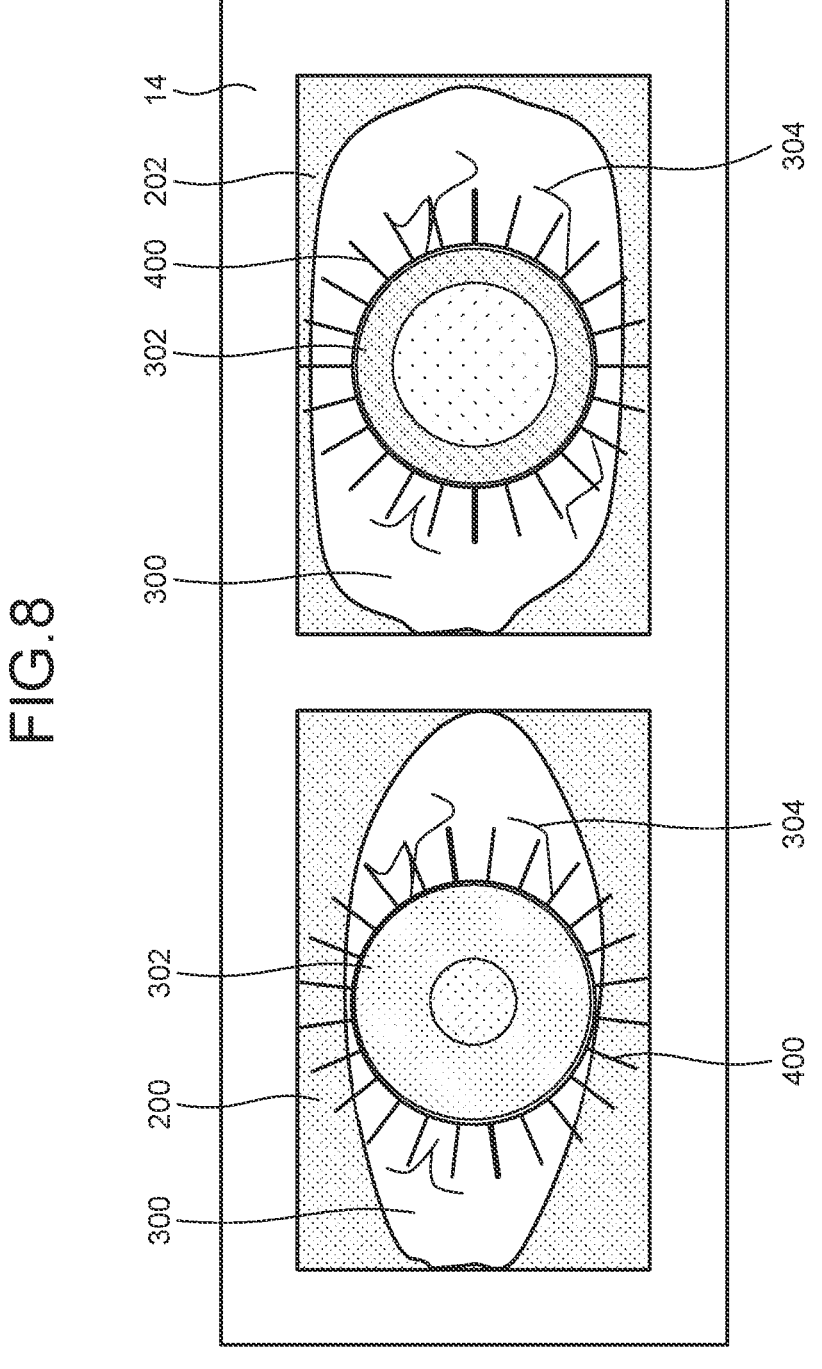
FIG. 8 is a view illustrating an example (Part 4) of a displayed image according to the first embodiment of the present disclosure.

Next, an example of a display screen in the present embodiment will be described with reference to FIGS. 5 to 8. FIGS. 5 to 8 are views illustrating examples of a displayed image according to the present embodiment. Specifically, FIGS. 5 and 6 are images provided before the above-described image processing method is performed, and FIGS. 7 and 8 are images provided after the above-described image processing method is performed.

First, before the above-described image processing method is performed, the image processing device 13 causes the monitor 14 to display an image of an eyeball 300 of a patient during preoperative planning as a preoperative image 200 and an image of the eyeball 300 of the patient at the start of surgery as an intraoperative image 202, as illustrated in FIG. 5.

Further, in the example of FIG. 5, the preoperative image 200 and the intraoperative image 202 are displayed so as to be arranged along the horizontal direction of the display screen of the monitor 14. Moreover, in FIG. 5, on each of the images 200 and 202, reference coordinates 400 that have an origin at the center of a corneal contour 302 of the eyeball 300 and have a plurality of graduations (graduations like those of a protractor) along a circular ring are superimposed and displayed. Note that, in FIG. 5, the ring of the reference coordinates 400 is superimposed and displayed along the corneal contour 302, but the ring of the reference coordinates 400 is not necessarily required to be superimposed and displayed along the corneal contour 302 in the present embodiment. Further, in the present embodiment, the position of the origin of the reference coordinates 400 is not limited to the center of the corneal contour 302, and the origin may be positioned at the pupil center, the corneal vertex, or the like. However, in the present embodiment, it is preferable to select the form, scale, position, orientation, and the like of the reference coordinates 400 such that a pattern 304 of a blood vessel, a scar, or the like outside the corneal contour 302 can be recognized.

Moreover, in the present embodiment, as illustrated in FIG. 6, the preoperative image 200 and the intraoperative image 202 may be displayed so as to be arranged along the longitudinal direction of the display screen of the monitor 14 in accordance with the preference of the operator, the operative method, or the like. As described above, in the present embodiment, when the two operative-field images (the preoperative image 200 and the intraoperative image 202) are arranged along the longitudinal direction, it is preferable that the respective origins of the reference coordinates on the two operative-field images are positioned on the same straight line along the longitudinal direction. On the other hand, in the present embodiment, when the two operative-field images are arranged along the horizontal direction, it is preferable that the respective origins of the reference coordinates on the two operative-field images are positioned on the same straight line along the horizontal direction. In this manner, in the present embodiment, the positions of the respective origins of the reference coordinates in the two operative-field images are matched, which makes it easy to grasp a feature point, such as a scar or a blood vessel, common to the two operative-field images.

Then, after the above-described image processing method is performed, the image processing device 13 causes the monitor 14 to display an image of the eyeball 300 of the patient at the time of preoperative planning as the preoperative image 200 and an image of the eyeball 300 of the patient at the start of surgery as the intraoperative image 202, as illustrated in FIG. 7. In the example of FIG. 7, the preoperative image 200 is turned with reference to the gradations of the reference coordinates 400, and thus the orientations of the preoperative image 200 and the intraoperative image 202 are matched. Note that, in the example of FIG. 7, the reference coordinates 400 on the preoperative image 200 are turned in accordance with turning of the preoperative image 200.

Note that, in the present embodiment, the operative-field images (the preoperative image 200 and the intraoperative image 202) are not necessarily required to be subjected to processing such as turning so that the scales, positions, and orientations of the preoperative image 200 and the intraoperative image 202 are matched as illustrated in FIG. 7. In the present embodiment, the position, orientation, and the like of the characteristic pattern 304 of a blood vessel, a scar, or the like can be grasped from the relative positional relationship with the reference coordinates 400, and hence the reference coordinates 400 may be subjected to processing such as turning as illustrated in FIG. 8. More specifically, in the example of FIG. 8, the image processing device 13 turns the reference coordinates 400 on the preoperative image 200, to match the respective orientations of the reference coordinates 400 of the preoperative image 200 and the intraoperative image 202. Note that, in the example of FIG. 8, the preoperative image 200 is not turned.

As described above, in the present embodiment, the postures (scales (sizes), positions, orientations, and the like) of the preoperative image 200 and the intraoperative image 202, and the postures (scales, positions, orientations, and the like) of the reference coordinates superimposed on those operative-field images (the preoperative image 200 and the intraoperative image 202) are matched on the basis of the registration information. Further, in the present embodiment, the two operative-field images having been subjected to the image processing in the above-described manner are arranged and displayed. Therefore, according to the present embodiment, the preoperative image 200 and the intraoperative image 202 are arranged and displayed, which allows the operator to easily grasp the position, the orientation, and the like of the common pattern 304 of a blood vessel or a scar of the eyeball 300 of the patient in each of the operative-field images 200 and 202. Further, in the present embodiment, the common reference coordinates 400 are displayed while being superimposed on the preoperative image 200 and the intraoperative image 202, which allows the operator to more easily grasp the position, orientation, and the like of the pattern 304 of a blood vessel or a scar of the eyeball 300 of the patient using the reference coordinates 400 as a reference. Consequently, according to the present embodiment, the operator can easily and accurately check whether the preoperative image 200 and the intraoperative image 202 are appropriately aligned.

<2.3 Modifications>

Next, examples of a display screen in modifications of the present embodiment will be described with reference to FIGS. 9 to 13. FIGS. 9 to 13 are views illustrating examples of a displayed image according to the modifications of the present embodiment.

Figure 9:
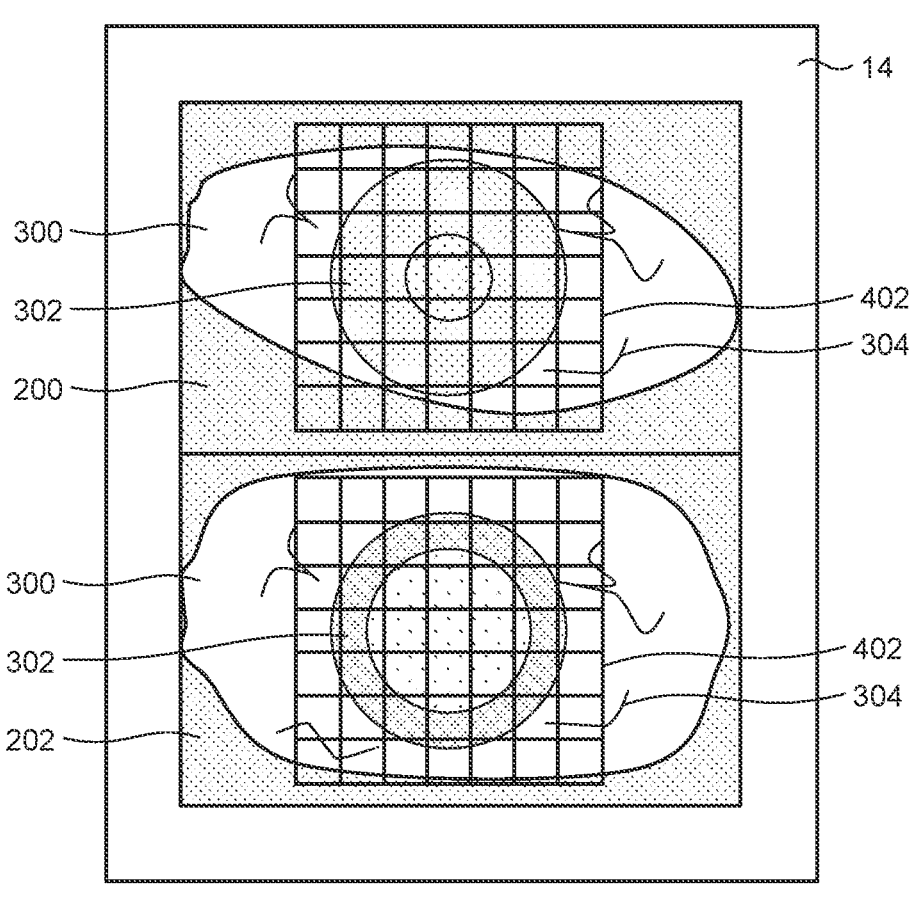
FIG. 9 is a view illustrating an example (Part 1) of a displayed image according to a modification of the first embodiment of the present disclosure.

For example, according to a modification of the present embodiment, as illustrated in FIG. 9, reference coordinates 402 superimposed and displayed on the preoperative image 200 and the intraoperative image 202 may be a grid representing XY coordinates. Note that, in the present modification, the reference coordinates 402 are not limited to a grid having rectangular cells as illustrated in FIG. 9, and may be, for example, a grid having triangular or polygonal cells.

Figure 10:
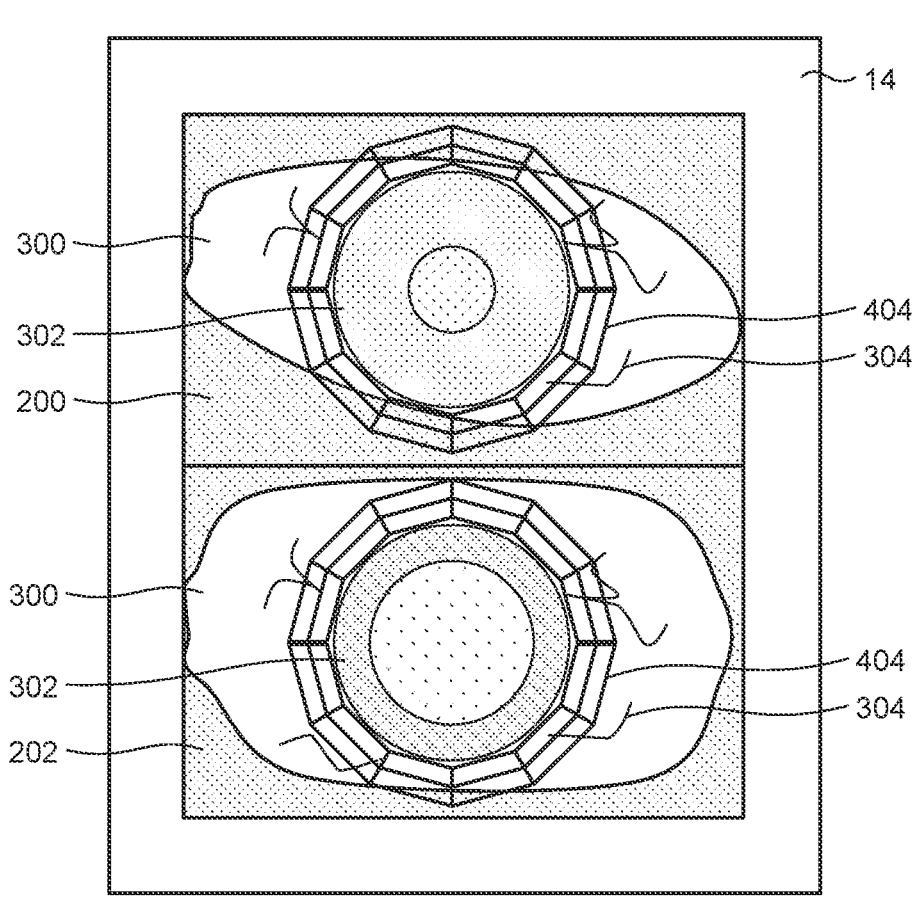
FIG. 10 is a view illustrating an example (Part 2) of a displayed image according to a modification of the first embodiment of the present disclosure.
Figure 11:
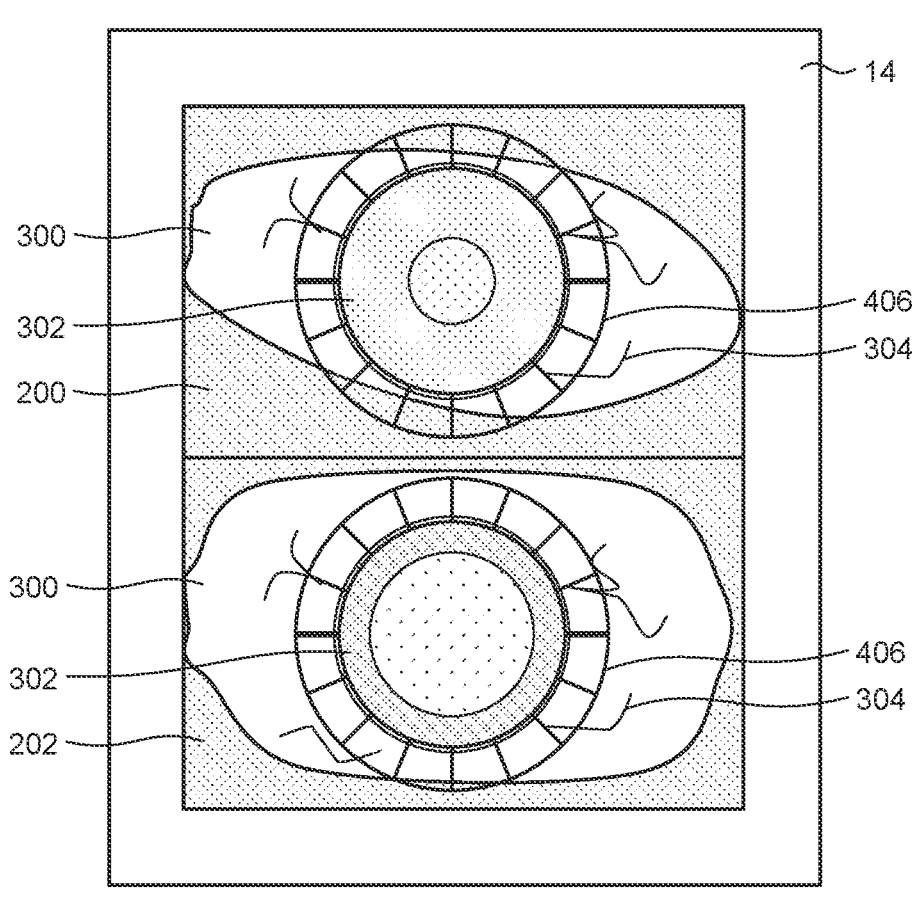
FIG. 11 is a view illustrating an example (Part 3) of a displayed image according to a modification of the first embodiment of the present disclosure.

Further, for example, according to a modification of the present embodiment, as illustrated in FIG. 10, reference coordinates 404 superimposed and displayed on the preoperative image 200 and the intraoperative image 202 may be a polygonal ring surrounding the corneal contour 302 of the eyeball 300, or coordinates having a spider-web grid. Moreover, according to a modification of the present embodiment, as illustrated in FIG. 11, reference coordinates 406 superimposed and displayed on the preoperative image 200 and the intraoperative image 202 may be polar coordinates formed of a circular ring surrounding the corneal contour 302 of the eyeball 300.

As described above, in the modifications of the present embodiment, it is possible to select one of the reference coordinates 400, 402, 404, and 406 having various forms, in accordance with the preference of the operator, the operative method, the pattern 304 of a blood vessel or a scar on the eyeball 300, and the like.

Figure 12:
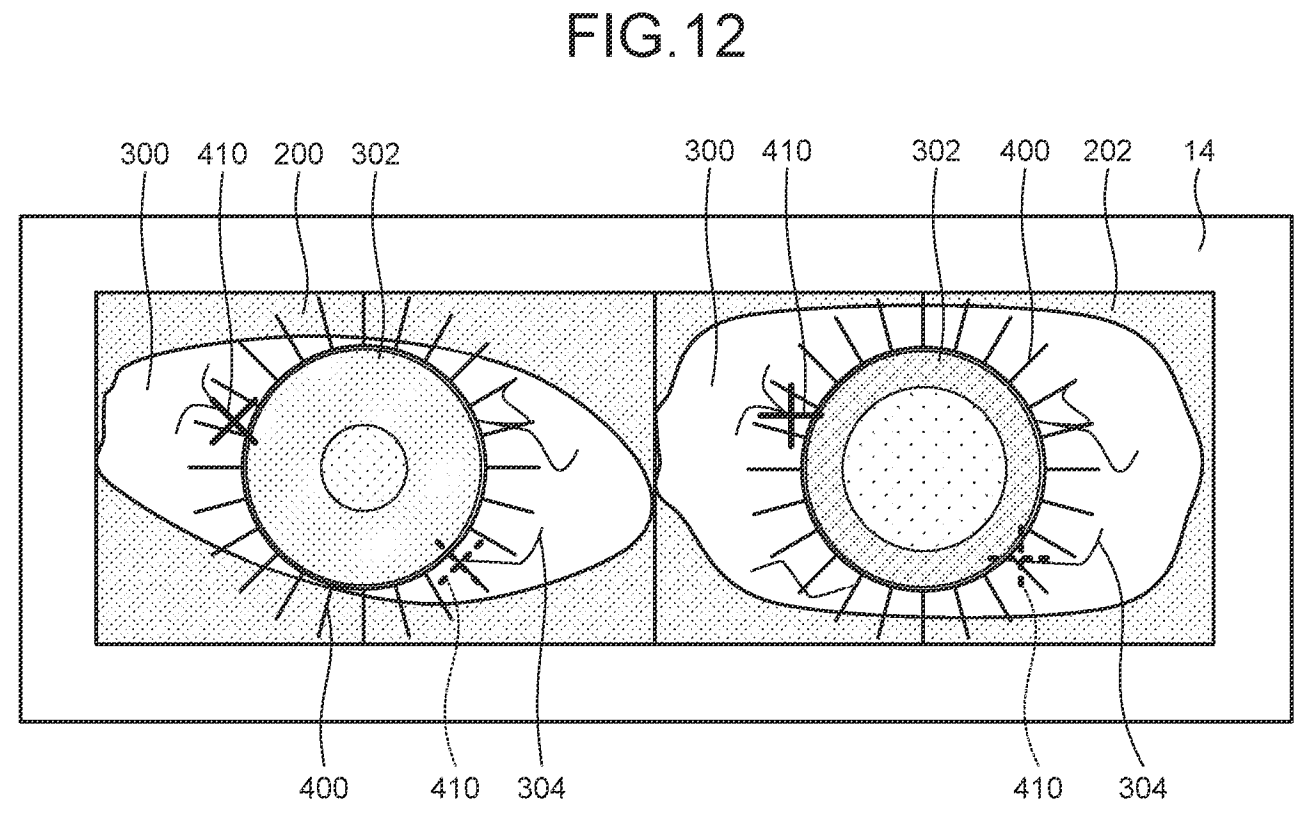

Further, according to a modification of the present embodiment, as illustrated in FIG. 12, a mark 410 may be superimposed and displayed on the pattern 304 (feature point) of a blood vessel or a scar in each of the two operative-field images so that the correspondence between the patterns 304 of a blood vessel or a scar common to the two operative-field images (the preoperative image 200 and the intraoperative image 202) can be easily grasped. In the present modification, the position of the mark 410 may be set, for example, by the operator in Step S105 described above, or may be set when a feature point common to the two operative-field images is extracted by image recognition in order to acquire the registration information. In the present modification, the mark 410 is superimposed and displayed on the pattern 304 of a blood vessel or a scar, and thus the operator can grasp at a glance the degree of matching of the plurality of common patterns 304 without depending on the memory.

Figure 13:
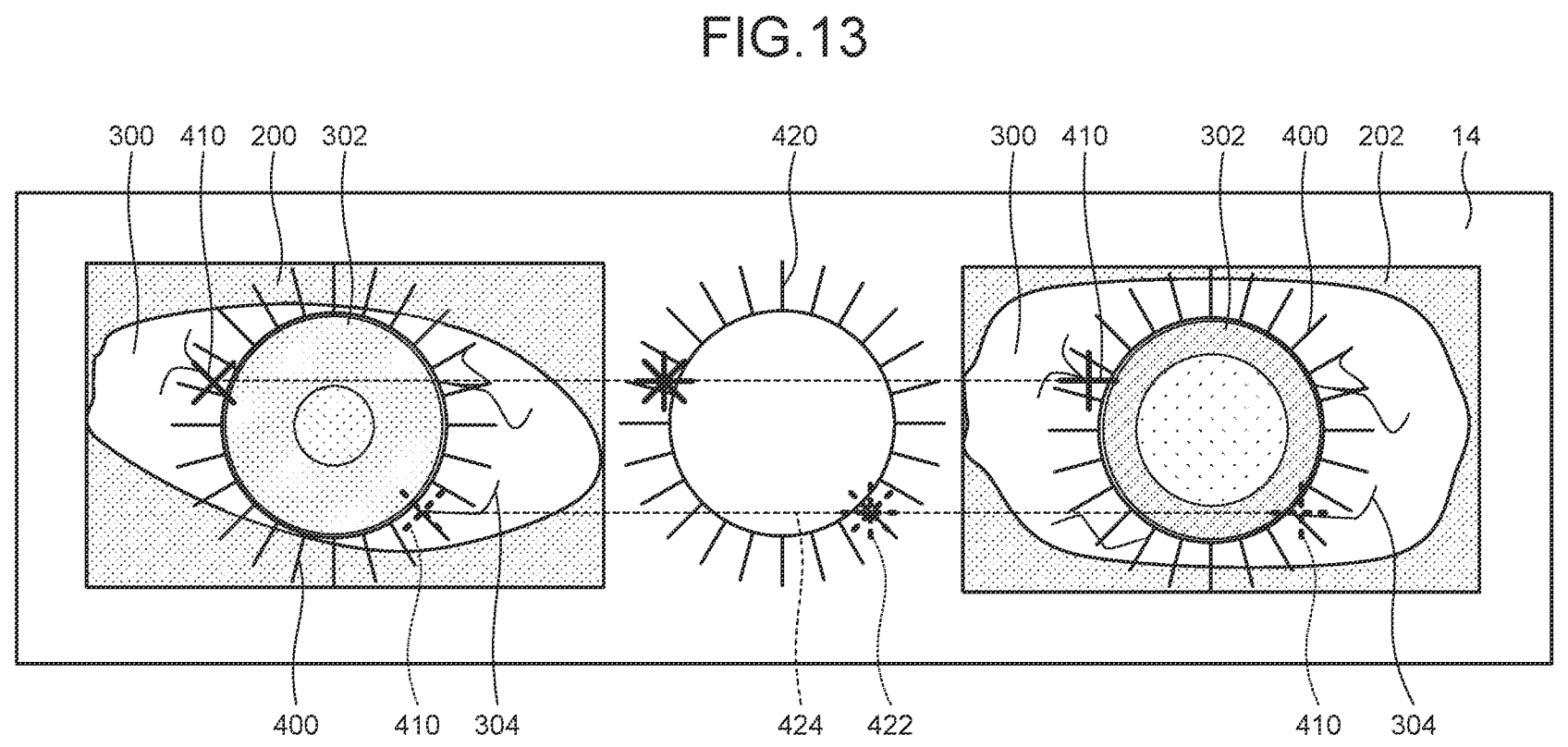

In addition, as the number of the patterns 304 of a blood vessel or a scar common to the two operative-field images (the preoperative image 200 and the intraoperative image 202) increases, it becomes more difficult to accurately grasp the correspondences thereof. Then, in the present modification, as illustrated in FIG. 13, reference coordinates (third reference image) 420 in the same form as the reference coordinates 400 superimposed on the two operative-field images are displayed between the preoperative image 200 and the intraoperative image 202. Further, in the present modification, also a mark 422 is superimposed and displayed on the reference coordinates 420. At that time, the number of the marks 422 in the reference coordinates 420 corresponds to the total number of marks 410 put on each of the preoperative image 200 and the intraoperative image 202. Further, the positions of the marks 422 are set so as to have the same relative positional relationship as that between the marks 410 put on each of the preoperative image 200 and the intraoperative image 202 and the reference coordinates 400. Therefore, on condition that the preoperative image 200 and the intraoperative image 202 have the same relative positional relationship between the marks 410 and the reference coordinates 400, the two marks 422 each corresponding to the mark 410 on the reference coordinates 420 should overlap each other.

As described above, in the present modification, it is possible to check at a glance whether the respective patterns 304 in the two operative-field images (the preoperative image 200 and the intraoperative image 202) correspond to each other by referring to the degree of overlapping of the marks 422 in the reference coordinates 420. Further, in the example of FIG. 13, lines 424 connecting the marks 410 and the marks 422 are also drawn in order to facilitate visual recognition of the correspondence between the mark 410 in each operative-field image and the mark 422 in the reference coordinates 420.

Note that, in the present embodiment and the present modifications, the form of the display screen is not limited to the examples illustrated in FIGS. 5 to 13, and various modifications are possible.

3. Second Embodiment

Figure 14:
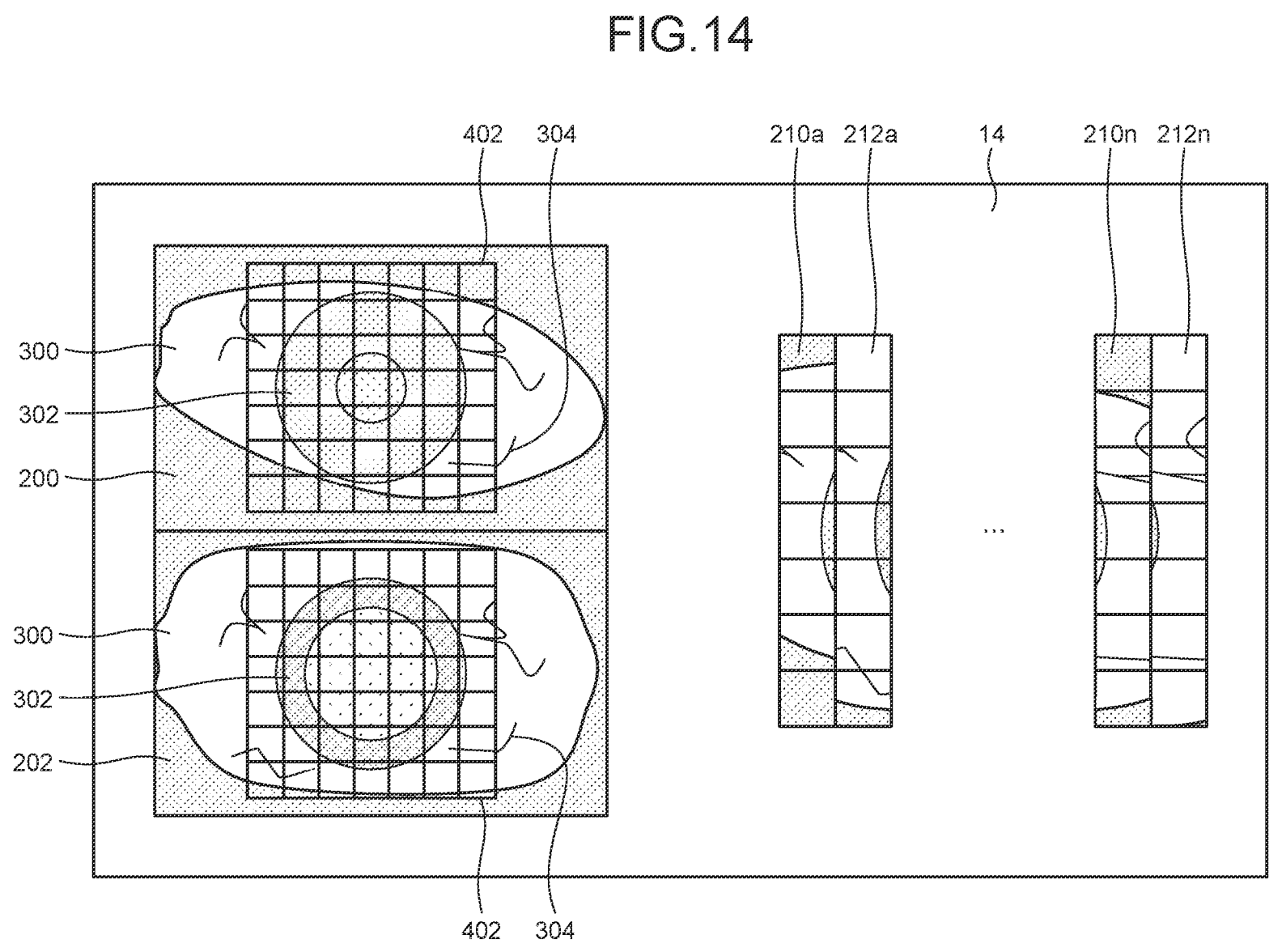
Figure 15:
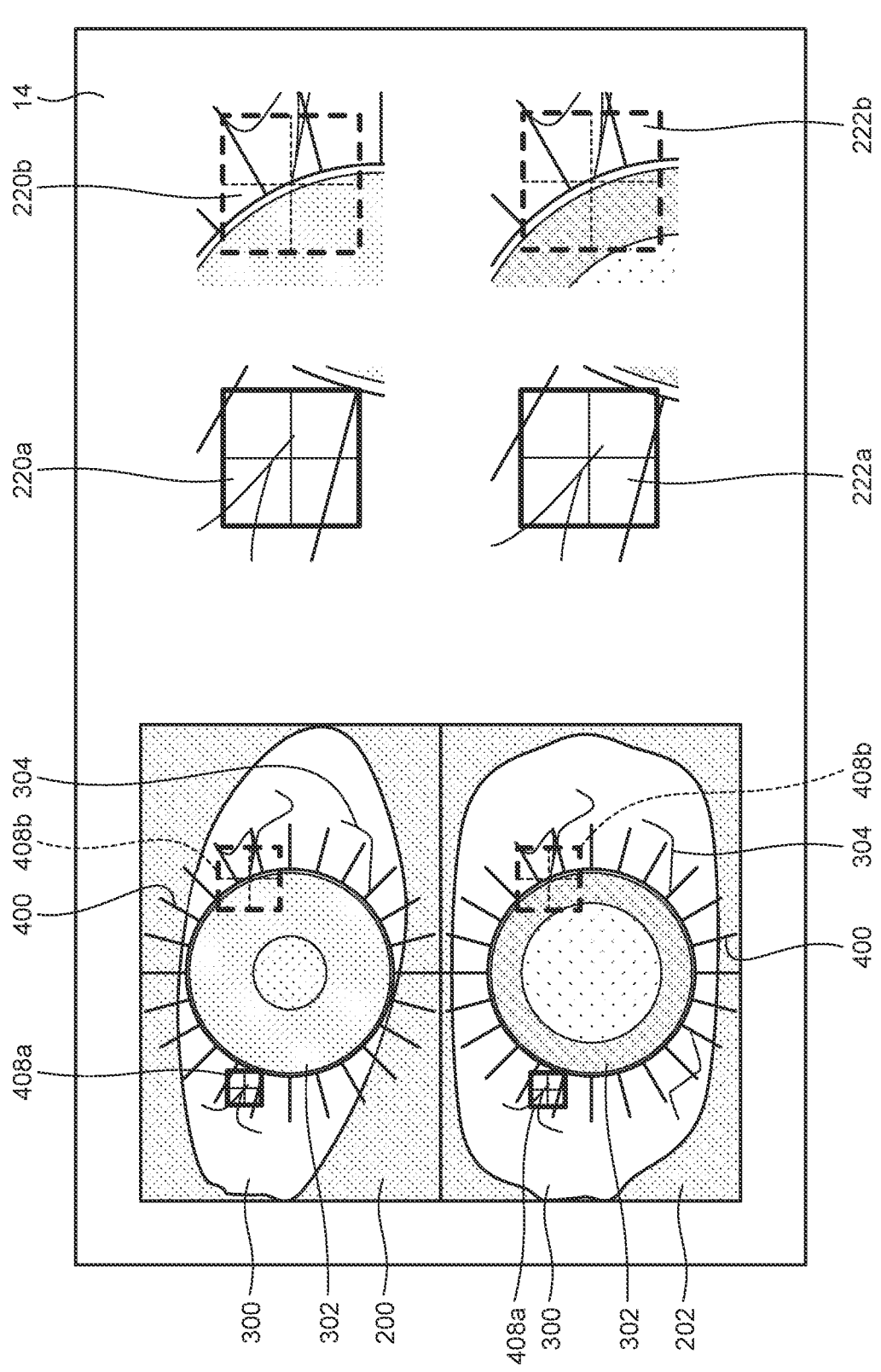
FIG. 15 is a view illustrating an example (Part 2) of a displayed image according to the second embodiment of the present disclosure.
Figure 16:
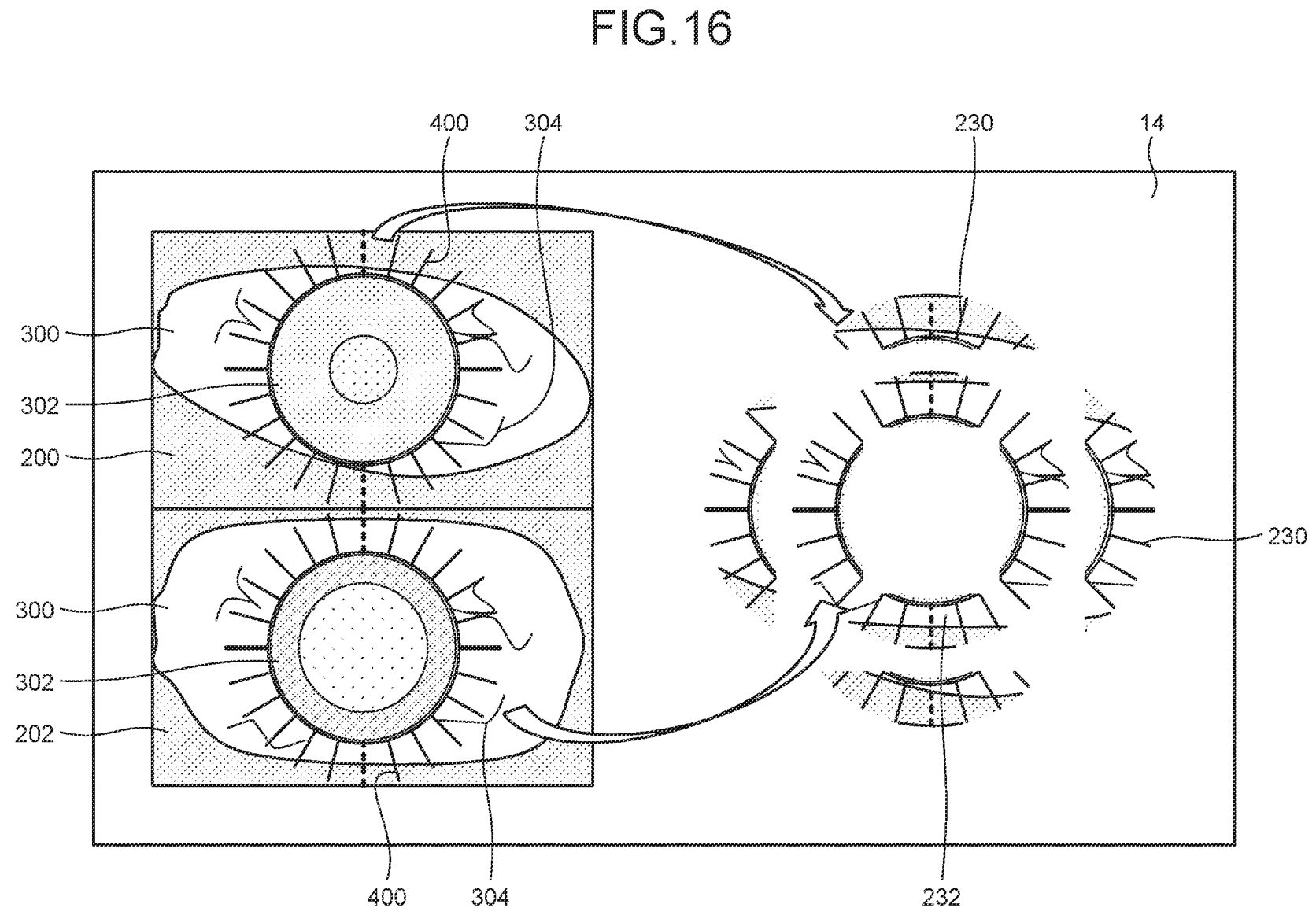

Next, an example of a display screen according to a second embodiment of the present disclosure will be described with reference to FIGS. 14 to 16. FIGS. 14 to 16 are views illustrating examples of a displayed image according to the present embodiment. Note that the displayed image according to the second embodiment of the present disclosure is displayed after being subjected to image processing in the above-described image processing device 13 according to the embodiments of the present disclosure.

In the first embodiment of the present disclosure described above, only an image of the entire eyeball 300 of the patient is provided. However, only with such an image of the entire eyeball 300, it is difficult to visually recognize the fine pattern 304 of a blood vessel, a scar, or the like on the eyeball 300 in some cases.

Further, the preoperative image 200 and the intraoperative image 202 are arranged and displayed, which requires the operator to move the line of sight between the two operative-field images (the preoperative image 200 and the intraoperative image 202) in order to grasp the correspondence between the respective patterns 304 of a blood vessel, a scar, or the like, for example. This probably results in an increase of a distance of line-of-sight movement. Then, due to the increase of a distance of line-of-sight movement, it becomes probably difficult to grasp the correspondence between of the above-described patterns 304, or it probably takes time to check the correspondence.

Then, in the present embodiment, a region of interest (ROI) common to the preoperative image 200 and the intraoperative image 202 is extracted from each of the images, and the two extracted ROIs are displayed while being arranged close to each other. In this manner, according to the present embodiment, it becomes easy to visually recognize the fine pattern 304, and an increase of a distance of line-of-sight movement can be reduced. Note that a plurality of ROIs may be extracted from each operative-field image.

Specifically, in the present embodiment, the image processing device 13 extracts, for example, all ROIs 210a to 210n each including the pattern 304 of a blood vessel, a scar, or the like from the preoperative image 200 using the grid of the reference coordinates 402 superimposed on the preoperative image 200 and the intraoperative image 202. Likewise, for example, all ROIs 212a to 212n each including the pattern 304 are extracted from the intraoperative image 202. Then, as illustrated in FIG. 14, the image processing device 13 displays the ROIs 210a and 212a, and the ROIs 210n and 212n, that respectively correspond to each other in position, adjacently to each other. Specifically, in the present embodiment, the ROIs 210 and 212 corresponding to each other are arranged adjacently to each other, in other words, the ROIs 210 of the preoperative image 200 and the ROIs 212 of the intraoperative image 202 are arranged such that they alternate. In this manner, according to the present embodiment, it becomes easy to visually recognize the fine pattern 304, and an increase of a distance of line-of-sight movement can be reduced.

Further, in the present embodiment, instead of extracting all the ROIs 210 and 212 each including the pattern 304 of a blood vessel, a scar, or the like, one or a plurality of ROIs 408a and 408b may be set in the preoperative image 200 and the intraoperative image 202. In the present embodiment, the above-described ROIs 408a and 408b can be set by the operator's selection of a randomly-selected position and range in one of the two operative-field images (the preoperative image 200 and the intraoperative image 202). Alternatively, the above-described ROIs 408a and 408b may be automatically set on the basis of a result of image recognition of the pattern 304 of a blood vessel, a scar, or the like.

Then, in the present embodiment, the image processing device 13 extracts the images in the ROIs 408a and 408b set in the preoperative image 200, as ROIs 220a and 220b. Likewise, the image processing device 13 extracts the images in the ROIs 408a and 408b set in the intraoperative image 202, as ROIs 222a and 222b. Further, as illustrated in FIG. 15, the image processing device 13 displays the ROIs 220a and 222a and the ROIs 220b and 222b that respectively correspond to each other in position, adjacently to each other. In this manner, according to the present embodiment, it becomes easy to visually recognize the fine pattern 304, and an increase of a distance of line-of-sight movement can be reduced.

Further, in the present embodiment, as illustrated in FIG. 16, ring-shaped (doughnut-shaped) ROIs 230 and 232 each surrounding the corneal contour 302 of the eyeball 300 may be set. Specifically, the ROI extracted from the preoperative image 200 is the ROI 230, and the ROI extracted from the intraoperative image 202 is the ROI 232. The ring-shaped ROIs 230 and 232 displayed in the above-described manner allow the operator to more intuitively grasp the position of the ROI in the eyeball 300, than a rectangular ROI. Note that, in the present embodiment, the shape of a ROI is not limited to a rectangular shape (or grid-like shape) or a ring shape.

Note that, in the present embodiment, the form of the display screen is not limited to the examples illustrated in FIGS. 14 to 16, and various modifications are possible. Further, in the present embodiment, the image extracted from each of the two operative-field images is not limited to an ROI, and an image in a preset range may be extracted, or a part or the whole of a preset operative-field image may be divided into a plurality of regions and extracted. In this case, the plurality of extracted regions are arranged such that the respective scales, positions, and orientations of the two operative-field images with respect to the respective reference coordinates correspond to each other.

4. Third Embodiment

Figure 17:
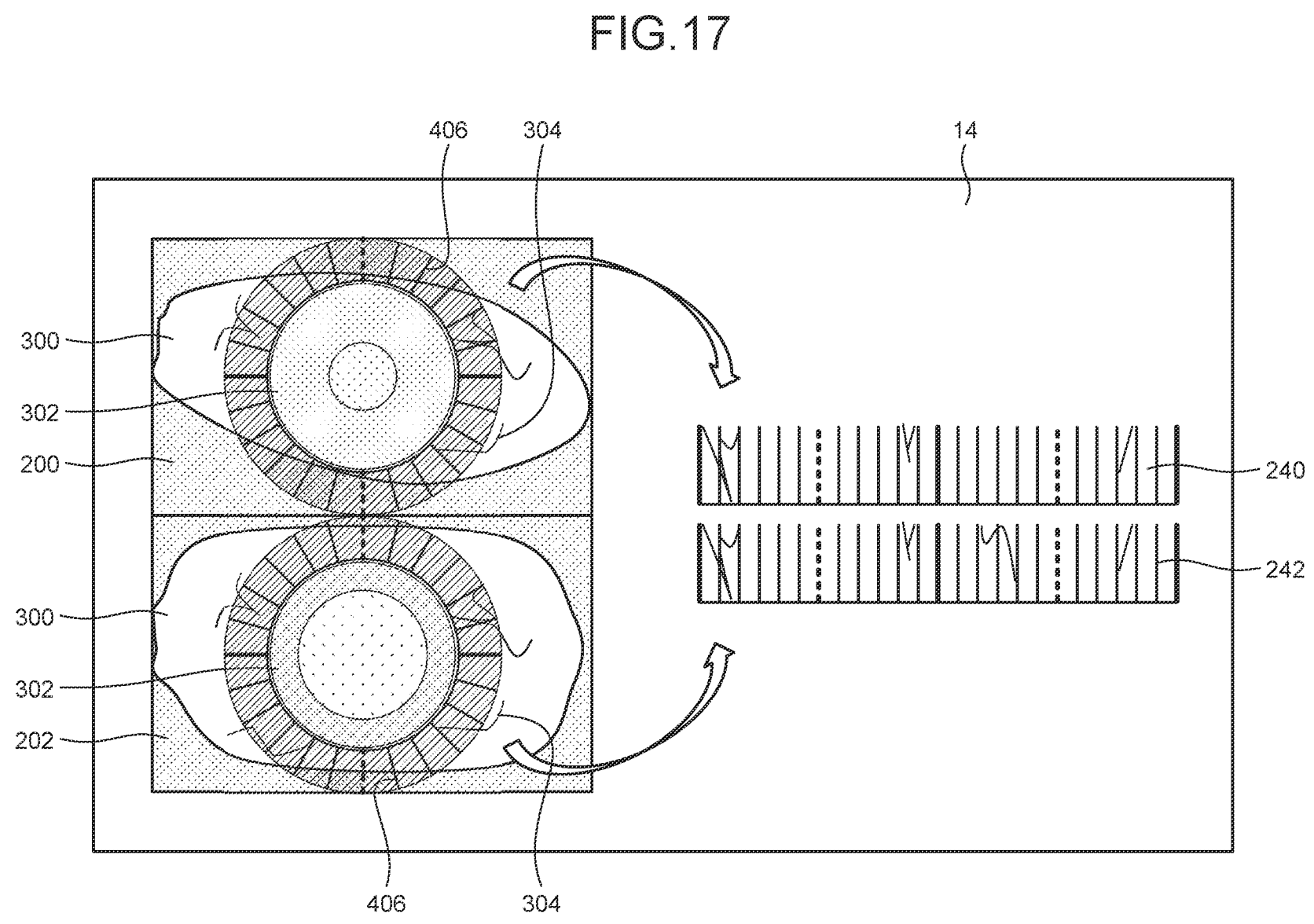
Figure 18:
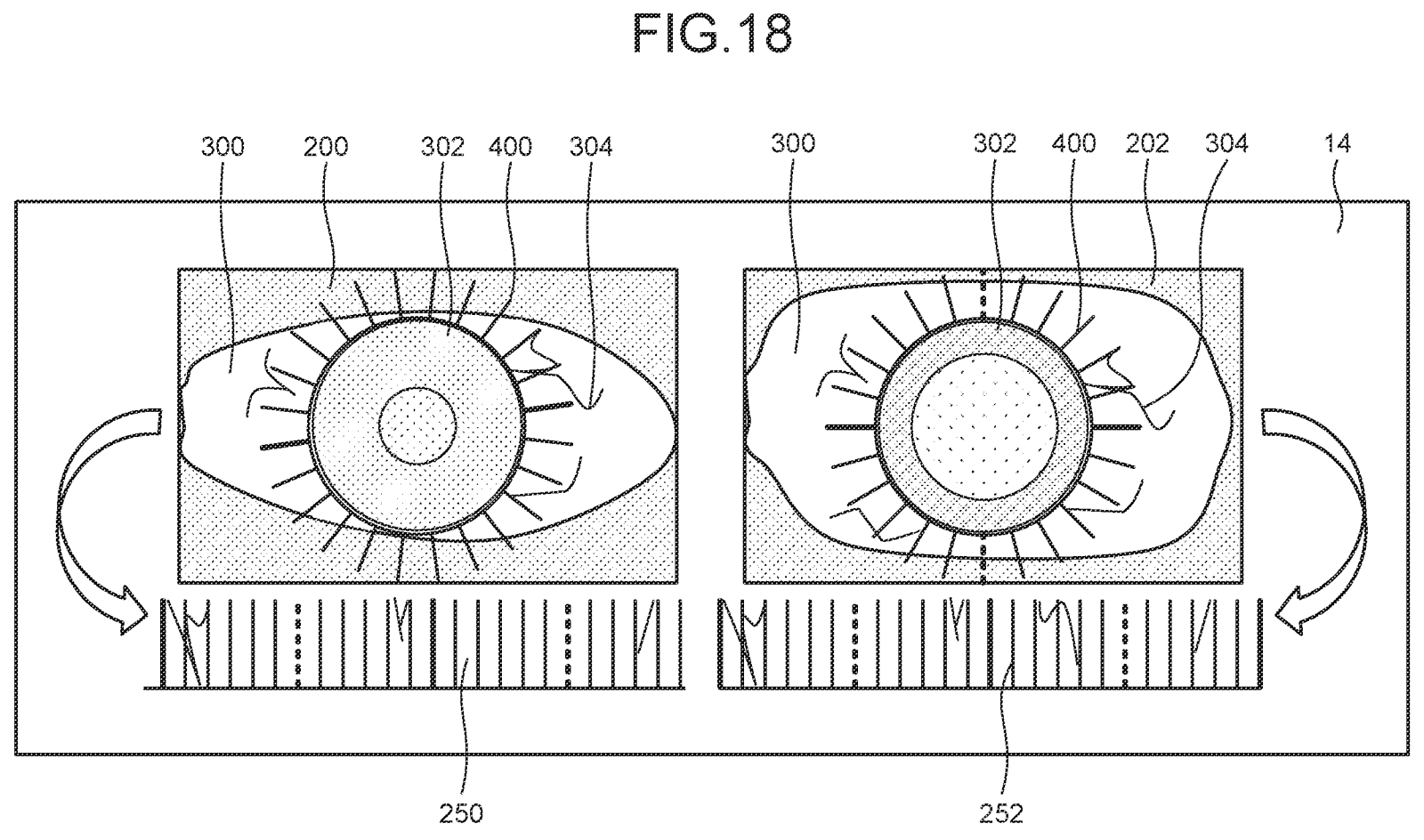

Next, examples of a display screen according to a third embodiment of the present disclosure will be described with reference to FIGS. 17 and 18. FIGS. 17 and 18 are views illustrating examples of a displayed image according to the present embodiment. Note that the displayed image according to the third embodiment of the present disclosure is displayed after being subjected to image processing in the above-described image processing device 13 according to the embodiments of the present disclosure.

First, in a displayed image illustrated in FIG. 17, ring-shaped reference coordinates 406 having an origin at the center of the corneal contour 302 of the eyeball 300 are displayed while being superimposed on the preoperative image 200 and the intraoperative image 202 that are turned so that the respective orientations match each other. Further, in the present embodiment, developed images 240 and 242 obtained by development of image regions overlapping the reference coordinates 406 into a band shape are displayed so as to be arranged along the longitudinal direction of the display screen of the monitor 14. Specifically, the developed image from the preoperative image 200 is the developed image 240, and the developed image from the intraoperative image 202 is the developed image 242. In the present embodiment, the preoperative image 200 and the intraoperative image 202 are not necessarily required to be turned, and may be translated, enlarged, or reduced. Alternatively, in the present embodiment, each of the preoperative image 200 and the intraoperative image 202 is not necessarily required to be at least partially divided into a plurality of regions and arranged after being adjusted such that the respective orientations match each other, to generate the developed images. For example, in the present embodiment, at least a part of each operative-field image before adjustment may be divided into a plurality of regions, and each region may be adjusted such that the respective scales and orientations of the operative-field images with respect to the reference image correspond to each other by turning, translation, enlargement, or reduction of each region, and then arranged, to generate the developed images.

Then, in each of the developed images 240 and 242 arranged along the longitudinal direction, the pattern 304 of a blood vessel, a scar, or the like is included in the same range of gradations, so that the operator can instantaneously grasp that the pattern 304 is common to the two operative-field images (the preoperative image 200 and the intraoperative image 202).

Further, in the present embodiment, the images are not necessarily required to be subjected to adjustment in which the respective orientations of the preoperative image 200 and the intraoperative image 202 are matched as illustrated in FIG. 17. In the present embodiment, for example, the reference coordinates 400 may be adjusted.

As illustrated in FIG. 18, the ring-shaped reference coordinates 400 having an origin at the center of the corneal contour 302 of the eyeball 300 are displayed while being superimposed on the preoperative image 200 and the intraoperative image 202, and the reference coordinates 400 on the preoperative image 200 are turned on the basis of the registration information. Then, in the example of FIG. 18, developed images 250 and 252 obtained by development of image regions overlapping the reference coordinates 400 into a band shape are displayed so as to be arranged along the horizontal direction of the display screen of the monitor 14. Specifically, the developed image from the preoperative image 200 is the developed image 250, and the developed image from the intraoperative image 202 is the developed image 252.

Then, in each of the developed images 250 and 252 arranged along the horizontal direction, the pattern 304 of a blood vessel, a scar, or the like is included in the same range of gradations, so that the operator can instantaneously grasp that the pattern 304 is common to the two operative-field images (the preoperative image 200 and the intraoperative image 202).

Note that, in the present embodiment, the form of the display screen is not limited to the examples illustrated in FIGS. 17 and 18, and various modifications are possible.

5. Conclusion

As described above, in each of the embodiments of the present disclosure, the postures (scales (sizes), positions, orientations, and the like) of the preoperative image 200 and the intraoperative image 202, and the postures (scales, positions, orientations, and the like) of the reference coordinates superimposed on those operative-field images (the preoperative image 200 and the intraoperative image 202) are matched on the basis of the registration information. Further, in the present embodiment, the two operative-field images having been subjected to the image processing in the above-described manner are arranged and displayed. Therefore, according to the present embodiment, the preoperative image 200 and the intraoperative image 202 are arranged and displayed, which allows the operator to easily grasp the position, the orientation, and the like of the common pattern 304 of a blood vessel or a scar of the eyeball 300 of the patient in each of the operative-field images 200 and 202. Further, in the present embodiment, the common reference coordinates 400 are displayed while being superimposed on the preoperative image 200 and the intraoperative image 202, which allows the operator to more easily grasp the position, orientation, and the like of the pattern 304 of a blood vessel or a scar of the eyeball 300 of the patient using the reference coordinates 400 as a reference. Consequently, according to the present embodiments, the operator can easily and accurately check whether the preoperative image 200 and the intraoperative image 202 are appropriately aligned. This results in reduction of time and effort for checking whether the position of an upper guide is appropriate, to thereby eliminate troubles of the operator.

Note that, in the embodiments of the present disclosure described above, an example has been described in which an image of the eyeball 300 of a patient who is yet to be subjected to surgery and an image of the eyeball 300 of the patient at the start of the surgery are arranged and displayed as the preoperative image 200 and the intraoperative image 202, respectively, but the images 200 and 202 are not limited to such images as mentioned. For example, in the embodiments of the present disclosure, an image of the eyeball 300 of a patient who is yet to be subjected to surgery and an image of the eyeball 300 of the patient who is undergoing the surgery may be arranged and displayed as the preoperative image 200 and the intraoperative image 202, respectively.

Further, in the embodiments of the present disclosure described above, an example applied to an ophthalmic surgery guidance has been described, but the present embodiments are not limited to application to such surgery. The present embodiments can be applied to any use in which it is required to closely check the respective postures (scales (sizes), positions, and orientations) of images match each other, for example.

6. Example of Schematic Configuration of Computer

The series of image processing steps in the embodiments of the present disclosure described above can be performed by hardware or software. In a case where the series of processing steps is performed by software, a program forming the software is installed in a computer. Here, examples of the computer include a computer incorporated in dedicated hardware, a computer capable of performing various functions by having various programs installed therein, such as a general-purpose computer, for example, and the like.

Figure 19:
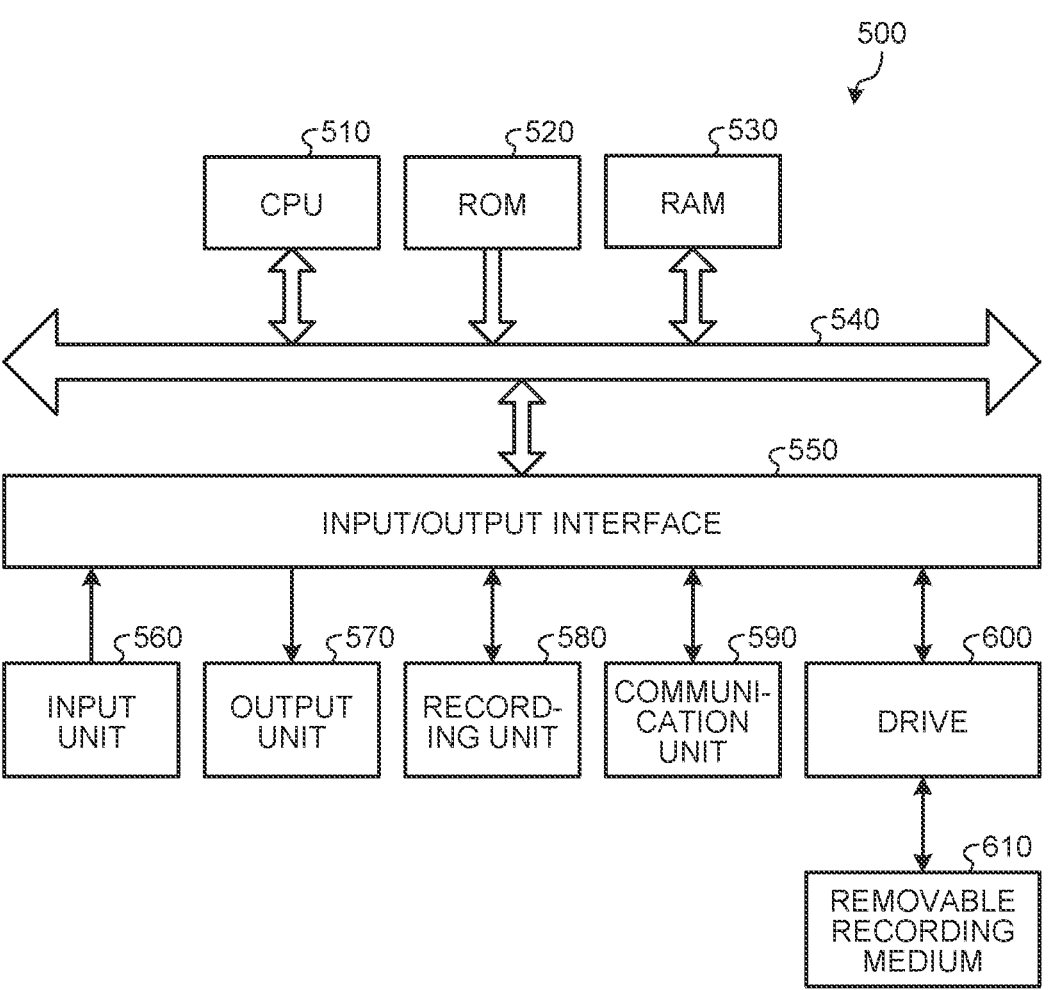
FIG. 19 is a view illustrating an example of a schematic configuration of a computer according to the embodiments of the present disclosure.

FIG. 19 is a view illustrating an example of a schematic configuration of a computer 500 that performs the above-described series of processing steps in accordance with a program.

As illustrated in FIG. 19, the computer 500 includes a central processing unit (CPU) 510, a read only memory (ROM) 520, and a random access memory (RAM) 530.

The CPU 510, the ROM 520, and the RAM 530 are connected to one another by a bus 540. The bus 540 is further connected to an input/output interface 550. The input/output interface 550 is connected to an input unit 560, an output unit 570, a recording unit 580, a communication unit 590, and a drive 600.

The input unit 560 includes a keyboard, a mouse, a microphone, an imaging element, and the like. The output unit 570 includes a display, a speaker, and the like. The recording unit 580 includes a hard disk, a nonvolatile memory, and the like. The communication unit 590 includes a network interface and the like. The drive 600 drives a removable recording medium 610 such as a magnetic disk, an optical disk, a magneto-optical disk, or a semiconductor memory.

In the computer 500 configured as described above, for example, the CPU 510 loads a program recorded in the recording unit 580 into the RAM 530 via the input/output interface 550 and the bus 540 and executes the program, whereby the above-described series of processing steps is performed.

It is possible to provide the program executed by the computer 500, that is, the CPU 510, by recording the program in the removable recording medium 610 as a package medium or the like, for example. Alternatively, it is possible to provide the program via a wired or wireless transmission medium such as a local area network, the Internet, or digital satellite broadcasting.

In the computer 500, the removable recording medium 610 is attached to the drive 600, and thus the program can be installed in the recording unit 580 via the input/output interface 550. Alternatively, the program can be received by the communication unit 590 via a wired or wireless transmission medium and installed in the recording unit 580. Further alternatively, the program can be installed in the ROM 520 or the recording unit 580 in advance.

Note that the program executed by the computer 500 may be a program in which processing is performed in a time series in the order described in the present specification, or may be a program in which processing is performed in parallel or at a requested time such as a time when a call is made. In addition, the computer 500 may have a cloud computing configuration in which one function is shared and cooperatively processed by a plurality of devices via a network.

7. Supplementary Notes

Note that the embodiments of the present disclosure described above can include, for example, an information processing method performed in the surgical microscope system 1 as described above, a program for causing the surgical microscope system 1 to function, and a non-transitory tangible medium in which the program is recorded. Further, the program may be distributed via a communication line (including wireless communication) such as the Internet.

Moreover, the respective steps in the processing of the embodiments of the present disclosure described above are not necessarily required to be performed in the described order. For example, the respective steps may be performed in an order that is appropriately modified. In addition, a part of the respective steps may be performed in parallel or individually, instead of being performed in a time series. Further, the processing of each step is not necessarily required to be performed according to the described method, and may be performed by another functional unit according to another method, for example.

Among the processing steps described in the above-described embodiments, all or a part of the processing steps described as being automatically performed can be manually performed, or all or a part of the processing steps described as being manually performed can be automatically performed by a known method. Besides, the processing procedure, the specific names, and the information including various data and parameters included in the above description and the drawings can be changed to any specific ones unless otherwise specified. For example, the various kinds of information illustrated in each of the drawings are not limited to the pieces of information illustrated.

Further, the components of each device illustrated in the drawings are only required to have the functions and concepts, and are not necessarily required to be physically configured as illustrated in the drawings. In other words, a specific form of separation and integration of each device is not limited to the illustrated form, and the whole or a part thereof can be separated or integrated functionally or physically in a randomly-selected unit depending on each load, each use condition, or the like.

Further, the effects described in the present specification are merely illustrative or exemplary, and are not restrictive. That is, the technology according to the present disclosure can produce other effects obvious to those skilled in the art from the description of the present specification, in addition to, or in place of, the above-described effects.

While the preferred embodiments of the present disclosure have been described above in detail with reference to the accompanying drawings, the technical scope of the present disclosure is not limited to the embodiments. It is obvious that a person having ordinary knowledge in the technical field of the present disclosure can conceive various changes or modifications within the scope of the technical idea described in the claims, and it is naturally understood that these also fall within the technical scope of the present disclosure.

Note that the present technology can also have the following configurations.

(1) An image processing device comprising a displayed-image generation unit configured to generate a displayed image in which a first reference image indicating reference coordinates of a preoperative image that is a captured image of an eyeball of a patient before surgery is superimposed on the preoperative image, and a second reference image indicating reference coordinates of an intraoperative image that is a captured image of the eyeball of the patient at the start of the surgery or during the surgery is superimposed on the intraoperative image, wherein the displayed-image generation unit arranges the first reference image and the second reference image such that the respective reference coordinates of the preoperative image and the intraoperative image correspond to each other, and such that a scale, a position, or an orientation of at least one of the preoperative image or the intraoperative image is changeable, to generate the displayed image.

(2) The image processing device according to (1), wherein the displayed-image generation unit arranges the preoperative image and the intraoperative image such that scales and orientations of the respective reference coordinates of the preoperative image and the intraoperative image match each other.

(3) The image processing device according to (1) or (2), wherein the displayed-image generation unit arranges the preoperative image and the intraoperative image along a longitudinal direction or a horizontal direction of a display screen.

(4) The image processing device according to any one of (1) to (3), wherein the displayed-image generation unit converts the preoperative image and the intraoperative image into a vascular structure image.

(5) The image processing device according to any one of (1) to (4), wherein the displayed-image generation unit turns, translates, enlarges, or reduces at least one of the preoperative image or the intraoperative image on the basis of an input operation performed by a user.

(6) The image processing device according to any one of (1) to (4), wherein the displayed-image generation unit turns, translates, enlarges, or reduces at least one of the preoperative image or the intraoperative image on the basis of a feature point that is acquired by image recognition and included on the preoperative image and the intraoperative image.

(7) The image processing device according to (6), wherein the displayed-image generation unit superimposes a mark on the feature point common to the preoperative image and the intraoperative image on the basis of a result obtained by image recognition performed on the preoperative image and the intraoperative image.

(8) The image processing device according to (6), wherein the displayed-image generation unit superimposes a mark on the feature point common to the preoperative image and the intraoperative image on the basis of an input operation performed by a user.

(9) The image processing device according to (7) or (8), wherein the displayed-image generation unit arranges a third reference image indicating a position of the feature point common to the preoperative image and the intraoperative image, between the preoperative image and the intraoperative image on which the first and second reference images are superimposed.

(10) The image processing device according to any one of (6) to (9), wherein the feature point is a pattern of a scar or a blood vessel of the eyeball of the patient.

(11) The image processing device according to any one of (1) to (10), wherein the displayed-image generation unit adjusts contrast, sharpness, brightness, or color of at least one of the preoperative image or the intraoperative image on the basis of a result obtained by image recognition performed on the preoperative image and the intraoperative image.

(12) The image processing device according to any one of (1) to (11), wherein the first and second reference images include polar coordinates having a plurality of graduations along a circular ring, or coordinates having a polygonal grid or a spider-web grid.

(13) The image processing device according to (1), wherein
the displayed-image generation unit divides at least a part of each of the preoperative image and the intraoperative image into a plurality of regions, and
the displayed-image generation unit arranges the regions of each of the preoperative image and the intraoperative image such that the respective scales, the respective positions, and the respective orientations of the preoperative image and the intraoperative image with respect to the respective reference coordinates, correspond to each other.

(14) The image processing device according to (13), wherein the displayed-image generation unit arranges the plurality of regions in a ring shape or a grid shape.

(15) The image processing device according to (1), wherein the displayed-image generation unit extracts a region of interest from each of the preoperative image and the intraoperative image, and arranges the regions of interest at corresponding positions, adjacently to each other.

(16) The image processing device according to (15), wherein the displayed-image generation unit arranges the region of interest extracted from the preoperative image and the region of interest extracted from the intraoperative image such that the regions of interest alternate.

(17) The image processing device according to (15) or (16), wherein the displayed-image generation unit extracts the region of interest on the basis of a result obtained by image recognition performed on the preoperative image and the intraoperative image.

(18) The image processing device according to (13), wherein the displayed-image generation unit arranges the regions in each of the preoperative image and the intraoperative image while adjusting a scale, a position, or an orientation of each of the regions such that the respective scales, the respective positions, and the respective orientations of the preoperative image and the intraoperative image with respect to the reference coordinates correspond to each other, to generate a developed image in which the plurality of regions in each of the preoperative image and the intraoperative image are arranged in a band shape.

(19) An image processing method comprising
generating, in an image processing device, a displayed image in which a first reference image indicating reference coordinates of a preoperative image that is a captured image of an eyeball of a patient before surgery is superimposed on the preoperative image, and a second reference image indicating reference coordinates of an intraoperative image that is a captured image of the eyeball of the patient at the start of the surgery or during the surgery is superimposed on the intraoperative image, wherein
the generating the displayed-image includes arranging the first reference image and the second reference image such that the respective reference coordinates of the preoperative image and the intraoperative image correspond to each other, and such that a scale, a position, or an orientation of at least one of the preoperative image or the intraoperative image is changeable, to generate the displayed image.

(20) A surgical microscope system comprising:
a surgical microscope configured to acquire an operative-field image for an eye of a patient;
an image processing device configured to generate a displayed image on the basis of the operative-field image; and
a display unit configured to display the displayed image, wherein
the image processing device includes
a displayed-image generation unit configured to generate the displayed image in which a first reference image indicating reference coordinates of a preoperative image that is a captured image of an eyeball of the patient before surgery is superimposed on the preoperative image, and a second reference image indicating reference coordinates of an intraoperative image that is a captured image of the eyeball of the patient at the start of the surgery or during the surgery is superimposed on the intraoperative image, and the displayed-image generation unit arranges the first reference image and the second reference image such that the respective reference coordinates of the preoperative image and the intraoperative image correspond to each other, and such that a scale, a position, or an orientation of at least one of the preoperative image or the intraoperative image is changeable, to generate the displayed image.

REFERENCE SIGNS LIST

1 SURGICAL MICROSCOPE SYSTEM
10 SURGICAL MICROSCOPE
11 OBJECTIVE LENS
12 EYEPIECE
13 IMAGE PROCESSING DEVICE
13A CONTROL UNIT
13a PREOPERATIVE-PLAN RECEIVING UNIT
13b IMAGE INPUT UNIT
13c REGISTRATION UNIT
13d INFORMATION ACCUMULATION UNIT
13e EYEBALL TRACKING UNIT
13f DISPLAYED-IMAGE GENERATION UNIT
14 MONITOR
20 PATIENT BED
51 LIGHT SOURCE
52 OBSERVATION OPTICAL SYSTEM
52a HALF MIRROR
53 FRONT IMAGE CAPTURING UNIT
54 TOMOGRAPHIC IMAGE CAPTURING UNIT
55 PRESENTATION UNIT
56 INTERFACE UNIT
57 SPEAKER
200 PREOPERATIVE IMAGE
202 INTRAOPERATIVE IMAGE
210a, 210n, 212a, 212n, 220a, 220b, 222a, 222b, 230, 232, 408a, 408b ROI
240, 242, 250, 252 DEVELOPED IMAGE
300 EYEBALL
302 CORNEAL CONTOUR
304 PATTERN
400, 402, 404, 406, 420 REFERENCE COORDINATES
410, 422 MARK
424 LINE

The invention claimed is:

1. An image processing device, comprising:
a displayed-image generation unit configured to:
arrange each of a first reference image, that indicates a first set of reference coordinates of a preoperative image, and a second reference image that indicates a second set of reference coordinates of an intraoperative image, wherein
the preoperative image is a first captured image of an eyeball of a patient before surgery,
the intraoperative image is a second captured image of the eyeball of the patient one of at a start of the surgery or during the surgery, and
the first reference image and the second reference image are arranged based on the first set of reference coordinates and the second set of reference coordinates;

generate a display image, based on the arrangement of the first reference image and the second reference image, in which the first reference image is superimposed on the preoperative image and the second reference image is superimposed on the intraoperative image, wherein
the first set of reference coordinates correspond to the second set of reference coordinates, and
at least one of a scale of at least one of the preoperative image or the intraoperative image, a position of the at least one of the preoperative image or the intraoperative image, or an orientation of the at least one of the preoperative image or the intraoperative image is changeable;
acquire at least one feature point of a plurality of feature points based on an image recognition operation on each of the preoperative image and the intraoperative image, wherein
the at least one feature point is on each of the preoperative image and the intraoperative image, and
the at least one feature point is common between the preoperative image and the intraoperative image;
superimpose a mark on the at least one feature point based on a result of the image recognition operation on each of the preoperative image and the intraoperative image; and
arrange a third reference image between the preoperative image on which the first reference image is superimposed in the generated display image, and the intraoperative image on which the second reference image is superimposed in the generated display image, wherein the third reference image indicates a position of the at least one feature point.

2. The image processing device according to claim 1, wherein the displayed-image generation unit is further configured to:
match a scale of the first set of reference coordinates of the preoperative image with a scale of the second set of reference coordinates of the intraoperative image;
match an orientation of the first set of reference coordinates of the preoperative image with an orientation of the second set of reference coordinates of the intraoperative image; and
arrange the preoperative image and the intraoperative image based on:
the match of the scale of the first set of reference coordinates with the scale of the second set of reference coordinates, and
the match of the orientation of the first set of reference coordinates with the orientation of the second set of reference coordinates.

3. The image processing device according to claim 1, wherein the displayed-image generation unit is further configured to arrange each of the preoperative image and the intraoperative image along one of a longitudinal direction of a display screen or a horizontal direction of the display screen.

4. The image processing device according to claim 1, wherein the displayed-image generation unit is further configured to convert each of the preoperative image and the intraoperative image into a vascular structure image.

5. The image processing device according to claim 1, wherein the displayed-image generation unit is further configured to at least one of turn, translate, enlarge, or reduce the at least one of the preoperative image or the intraoperative image based on one of the at least one feature point or a user operation.

6. The image processing device according to claim 1, wherein the displayed-image generation unit is further configured to superimpose the mark on the at least one feature point based on a user operation.

7. The image processing device according to claim 1, wherein the at least one feature point is a pattern of at least one of a scar of the eyeball of the patient or a blood vessel of the eyeball of the patient.

8. The image processing device according to claim 1, wherein the displayed-image generation unit is further configured to adjust, based on the result of the image recognition operation on each of the preoperative image and the intraoperative image, at least one of a contrast of the at least one of the preoperative image or the intraoperative image, a sharpness of the at least one of the preoperative image or the intraoperative image, a brightness of the at least one of the preoperative image or the intraoperative image, or a color of the at least one of the preoperative image or the intraoperative image.

9. The image processing device according to claim 1, wherein each of the first reference image and the second reference image includes one of a plurality of polar coordinates that includes a plurality of graduations along a circular ring, or a plurality of coordinates that includes one of a polygonal grid or a spider-web grid.

10. The image processing device according to claim 1, wherein the displayed-image generation unit is further configured to:

divide at least a part of each of the preoperative image and the intraoperative image into a plurality of regions; and arrange the plurality of regions of each of the preoperative image and the intraoperative image, wherein based on the arrangement of the plurality of regions, at least one of the scale of the preoperative image with respect to the first set of reference coordinates, the position of the preoperative image with respect to the first set of reference coordinates, or the orientation of the preoperative image with respect to the first set of reference coordinates corresponds to at least one of the scale of the intraoperative image with respect to the second set of reference coordinates, the position of the intraoperative image with respect to the second set of reference coordinates, or the orientation of the intraoperative image with respect to the second set of reference coordinates.

11. The image processing device according to claim 10, wherein the displayed-image generation unit is further configured to arrange the plurality of regions in at least one of a ring shape or a grid shape.

12. The image processing device according to claim 1, wherein the displayed-image generation unit is further configured to:

extract a first region of interest from the preoperative image;

extract a second region of interest from the intraoperative image; and arrange the first region of interest adjacent to the second region of interest at respective positions.

13. The image processing device according to claim 12, wherein the displayed-image generation unit is further configured to arrange the first region of interest and the second region of interest alternatively.

14. The image processing device according to claim 12, wherein the displayed-image generation unit is further configured to extract each of the first region of interest and the second region of interest based on the result of the image recognition operation on each of the preoperative image and the intraoperative image.

15. The image processing device according to claim 10, wherein the displayed-image generation unit is further configured to:

arrange the plurality of regions in each of the preoperative image and the intraoperative image in a band shape;

adjust at least one of a scale of each of the plurality of regions, a position of each of the plurality of regions, or an orientation of each of the plurality of regions;

based on the adjustment of the at least one of the scale of each of the plurality of regions, the position of each of the plurality of regions, or the orientation of each of the plurality of regions, at least one of the scale of the preoperative image with respect to the first set of reference coordinates, the position of the preoperative image with respect to the first set of reference coordinates, or the orientation of the preoperative image with respect to the first set of reference coordinates corresponds to at least one of the scale of the intraoperative image with respect to the second set of reference coordinates, the position of the intraoperative image with respect to the second set of reference coordinates, or the orientation of the intraoperative image with respect to the second set of reference coordinates; and generate a developed image that includes the plurality of regions, arranged in the band shape, in each of the preoperative image and the intraoperative image.

16. An image processing method, comprising:

in an image processing device, arranging each of a first reference image, that indicates a first set of reference coordinates of a preoperative image, and a second reference image that indicates a second set of reference coordinates of an intraoperative image, wherein the preoperative image is a first captured image of an eyeball of a patient before surgery, the intraoperative image is a second captured image of the eyeball of the patient one of at a start of the surgery or during the surgery, and the first reference image and the second reference image are arranged based on the first set of reference coordinates and the second set of reference coordinates;

generating a display image, based on the arrangement of the first reference image and the second reference image, in which the first reference image is superimposed on the preoperative image and the second reference image is superimposed on the intraoperative image, wherein the first set of reference coordinates correspond to the second set of reference coordinates, and at least one of a scale of at least one of the preoperative image or the intraoperative image, a position of the at least one of the preoperative image or the intraoperative image, or an orientation of the at least one of the preoperative image or the intraoperative image is changeable;

acquiring at least one feature point of a plurality of feature points based on an image recognition operation on each of the preoperative image and the intraoperative image, wherein the at least one feature point is on each of the preoperative image and the intraoperative image, and the at least one feature point is common between the preoperative image and the intraoperative image;

superimposing a mark on the at least one feature point based on a result of the image recognition operation on each of the preoperative image and the intraoperative image; and arranging a third reference image between the preoperative image, on which the first reference image is superimposed in the generated display image, and the intraoperative image on which the second reference image is superimposed, wherein the third reference image indicates a position of the at least one feature point.

17. A surgical microscope system, comprising:

a surgical microscope configured to acquire an operative-field image for an eye of a patient;

an image processing device configured to generate a display image based on the operative-field image; and a display unit configured to display the display image, wherein the image processing device includes a displayed-image generation unit that is configured to:

arrange each of a first reference image, that indicates a first set of reference coordinates of a preoperative image, and a second reference image that indicates a second set of reference coordinates of an intraoperative image, wherein the operative-field image includes the preoperative image and the intraoperative image, the preoperative image is a first captured image of an eyeball of the patient before surgery, the intraoperative image is a second captured image of the eyeball of the patient one of at a start of the surgery or during the surgery, and the first reference image and the second reference image are arranged based on the first set of reference coordinates and the second set of reference coordinates;

generate the display image, based on the arrangement of the first reference image and the second reference image, in which the first reference image is superimposed on the preoperative image and the second reference image is superimposed on the intraoperative image, wherein the first set of reference coordinates correspond to the second set of reference coordinates, and at least one of a scale of at least one of the preoperative image or the intraoperative image, a position of the at least one of the preoperative image or the intraoperative image, or an orientation of the at least one of the preoperative image or the intraoperative image is changeable;

acquire at least one feature point of a plurality of feature points based on an image recognition operation on each of the preoperative image and the intraoperative image, wherein the at least one feature point is on each of the preoperative image and the intraoperative image, and the at least one feature point is common between the preoperative image and the intraoperative image;

superimpose a mark on the at least one feature point based on a result of the image recognition operation on each of the preoperative image and the intraoperative image; and arrange a third reference image between the preoperative image, on which the first reference image is superimposed in the generated display image, and the intraoperative image on which the second reference image is superimposed, wherein the third reference image indicates a position of the at least one feature point.

* * * * *